(12) United States Patent
Schwink et al.

(10) Patent No.: US 7,763,740 B2
(45) Date of Patent: Jul. 27, 2010

(54) METHOD FOR THE PRODUCTION OF MUMBAISTATIN DERIVATIVES

(75) Inventors: Lothar Schwink, Stadtallendorf (DE); Gunther Schmalz, Bruhl (DE); David Sucunza, Logrono (ES); Janna Velder, Bruhl (DE); Daniel Dembkowski, Essen (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/250,705

(22) Filed: Oct. 14, 2008

(65) Prior Publication Data

US 2009/0156836 A1 Jun. 18, 2009

Related U.S. Application Data

(63) Continuation of application No. PCT/EP2007/002869, filed on Mar. 30, 2007.

(30) Foreign Application Priority Data

Apr. 19, 2006 (DE) .................. 10 2006 018 475

(51) Int. Cl.
*C07D 313/06* (2006.01)
*C07C 69/95* (2006.01)

(52) U.S. Cl. ...................... 549/268; 560/53
(58) Field of Classification Search ........... 549/268; 560/53
See application file for complete search history.

(56) References Cited

OTHER PUBLICATIONS

Diederichs XP-002440795, URL: http://www.meind.de/search.py?recid=260156.*
Uno et al.STN Accession No. 2000:651052; Document No. 133:335111, Abstract of Chemistry Letters (2000), (9), 1014-1015.*
Carreras et al. Journal of the American Chemical Society (1996), 118(21), 5158-5159.*
Uno et al. Chemistry Letters (2000), (9), 1014-1015.*
Bingham, S. J., et. al., The Synthesis of Kermesic Acid and Isokermesic Acid Derivatives and of Related Dihydroxyanthraquinones, Journal of the Chemical Society, Perkin Transactions 1: Organic and Bio-Organic Chemistry, vol. 24, pp. 3637-3642, (abstract) (1997).
Diederichs, J., et. al., Synthesis of Natural Chinoid Substances: A New Way to the 2'-Dialkyl-Mumbaistatin, (2005) No pp. given Avail.: Metadata on Internet Documents, Order No. 260156 From: Metadata Internet Doc. [Ger. Diss.] (2005), (D1031-4), No. pp. given URL: http://www/meind.de/search.py?recid=260156 (abstract).
Kaiser, F., et. al., Studies Towards the Total Synthesis of Mumbaistatin: Synthesis of Highly Substituted Benzophenone and Anthraquinone Building Blocks, Tetrahedron, vol. 59, (2003) pp. 3201-3217.

* cited by examiner

*Primary Examiner*—D. Margaret Seaman
*Assistant Examiner*—Nizal S Chandrakumar
(74) *Attorney, Agent, or Firm*—Jiang Lin

(57) ABSTRACT

The present invention relates to a process for preparing mumbaistatin derivatives (I), where the anthraquinone skeleton is constructed via a Diels-Alder reaction and the central methylene bridge via a transition metal-catalyzed reaction, and to the intermediates used in this process.

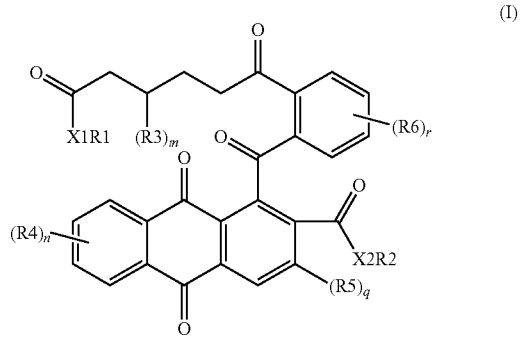

41 Claims, No Drawings

METHOD FOR THE PRODUCTION OF MUMBAISTATIN DERIVATIVES

This application is a Continuation of International Application No. PCT/EP2007/002869, filed Mar. 30, 2007, which is incorporated herein by reference in its entirety.

FIELD OF THE INVENTION

The present invention relates to processes for preparing mumbaistatin and mumbaistatin derivatives, and to the intermediates used in these processes.

BACKGROUND OF THE INVENTION

Mumbaistatin is an aromatic diketo derivative which, as glucose 6-phosphatase translocase inhibitor, can be used in the treatment of diabetes mellitus. Mumbaistatin (A) can be isolated from the microorganism DSM11641 (Vertesy et al., WO99/67408 and J. Antibiot. 2001, 54, 354-363). WO01/30736 describes the mumbaistatin derivatives (B)-(D) and esters and ethers thereof. Mumbaistatin is present in an equilibrium of an open form (A) and a hemiacetal form (B) and, depending on the pH, can be converted into the compounds (B) and (D).

(A)
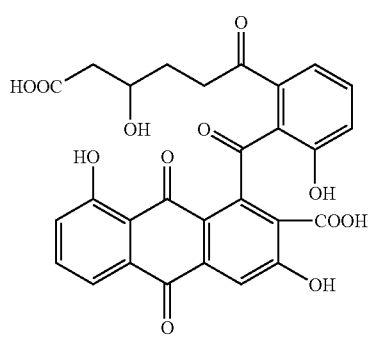

(B)
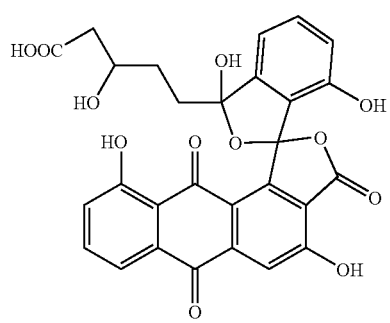

(C)
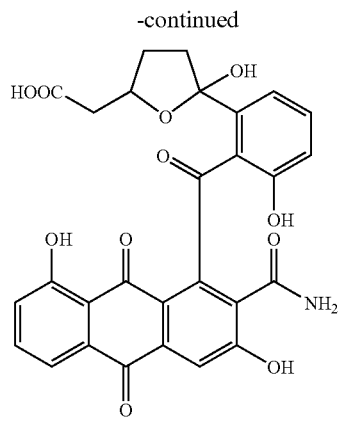

(D)
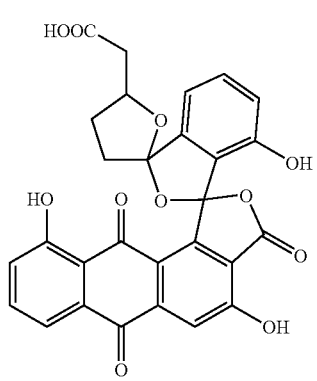

Krohn et al. (Tetrahedron 2006, 62, 1223-1230) describe a 7-9-step synthesis of the tri-ortho-substituted 2'-dealkyl mumbaistatin derivatives of the formula (E), where the oxidation of the benzylic position was effected using $Br_2$ in a $CCl_4$/water mixture with irradiation (E)
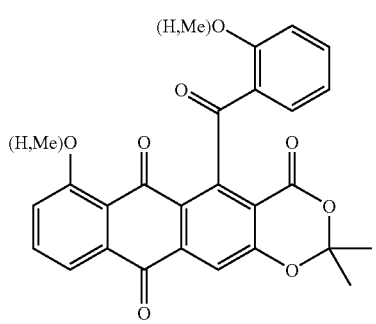

(F)
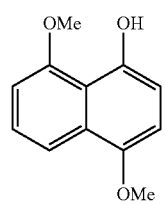

and where the anthraquinone skeleton is constructed by a multi-step aldol condensation of a diene intermediate prepared by a Lewis acid-catalyzed Michael addition, and the total yield starting from the naphthyl derivative (F) is from 2.8 to 14.1%.

Kaiser et al. (J. Org. Chem. 2002, 67, 9248-9256; Tetrahedron 2003, 59, 3201-3217) describe the 9-step synthesis of the tri-ortho-substituted 3'-deoxy-2-decarboxy mumbaistatin derivative (G),

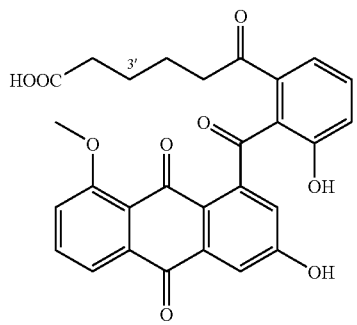

(G)

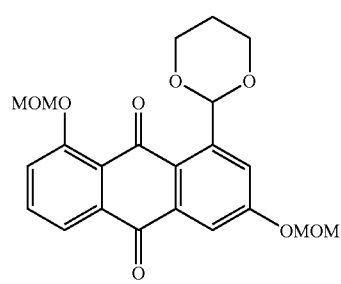

(H)

where the anthraquinone skeleton (H) was prepared via an aryne/phthalide anellation and the total yield starting from commercially available 3-hydroxybenzaldehyde is 3.7%.

It is the object of the present invention to provide an efficient synthesis route to mumbaistatin derivatives.

SUMMARY OF THE INVENTION

The present invention relates to a process for preparing mumbaistatin derivatives of the formula (I) or salts thereof,

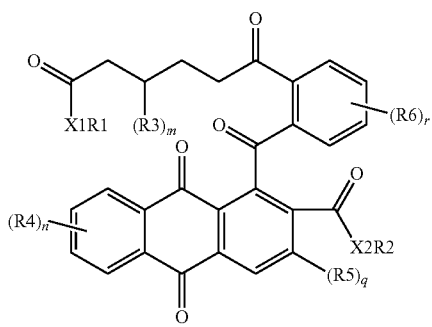

(I)

where
R1 and R2 independently of one another are H, $(C_1$-$C_6)$-alkyl or benzyl, R3, R4 and R5 independently of one another are OH, O—$(C_1$-$C_6)$-alkyl, O-benzyl or O-acyl,
R6 is OH, halogen, $(C_1$-$C_6)$-alkyl, O—$(C_1$-$C_6)$-alkyl, phenyl, benzyl, O-phenyl, O-benzyl, O-acyl,
X1 and X2 independently of one another are O, NH, N($C_1$-$C_6$)-alkyl or S, and m, n, q and r independently of one another are 0 or 1, where in step (1) a compound of the formula (II)

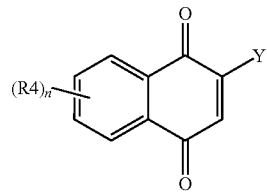

(II)

in which Y is a leaving group selected from the group consisting of Hal, OTs, OTf and OMs, and is preferably chlorine or bromine, is reacted with a compound of the formula (III),

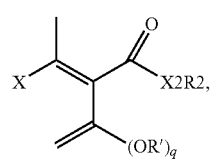

(III)

in which X is an electron-pushing group, for example [$(C_1$-$C_6)$-alkyl]$_3$silyloxy, preferably [methyl]$_3$silyloxy, and R' is $(C_1$-$C_6)$-alkyl or [$(C_1$-$C_6)$-alkyl]$_3$silyl, in a [2+4]cycloaddition and subsequently reacted with a suitable acid to give a compound of the formula (IV),

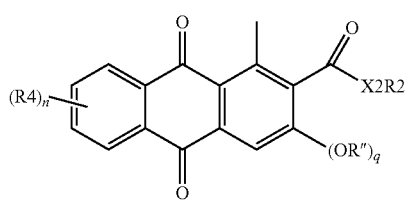

(IV)

where R''=H or $(C_1$-$C_6)$-alkyl, in step (2), if q=1 and R''=H, the phenolic OH group is optionally, under conditions known per se to the person skilled in the art, etherified with a $(C_1$-$C_6)$-alkyl halide compound or a benzyl halide compound or esterified with an acyl halide compound, and the compound (IV) or resulting etherified or acylated compound (IV) is then halogenated to give a compound of the formula (V),

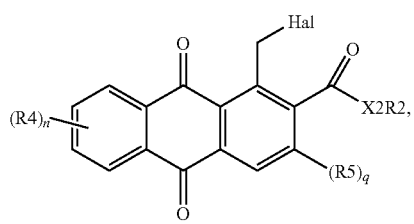

(V)

in step (3.1) the compound (V) is reacted with an organometallic compound (VI)

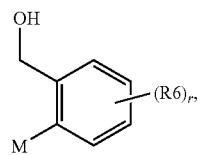
(VI)

in which M is $Sn[(C_1-C_6)\text{-alkyl}]_3^-$, $B(OH)_2$, $B(OR)_2$, $BF_3^-$, ZnHal or MgHal and $(OR)_2$ is $[O-(C_1-C_6)\text{-alkyl}]_2$ or a 1,2-vicinal diol, for example pinacol, catechol, where a boronic ester derived from the vicinal diol is formed, with transition metal catalysis, preferably with Pd, Ni or Fe catalysis, to give a compound of the formula (VII),

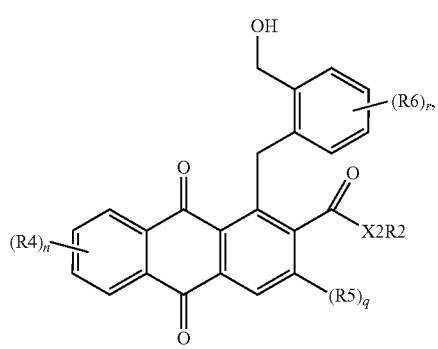
(VII)

followed by oxidation of the compound (VII) to a compound (VIII),

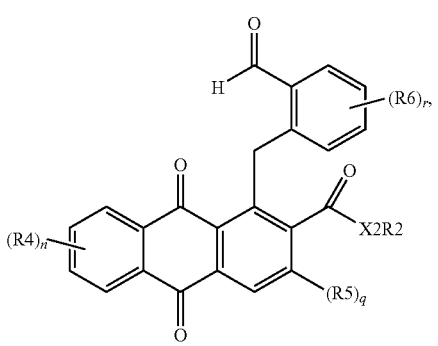
(VIII)

or alternatively, in a step (3.2), the compound (V) is reacted with an organometallic compound (VI')

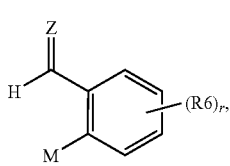
(VI')

where M and R6 are as defined for compound (VI) and Z is $O-(C_1-C_6)$-alkylene-O, preferably $O-(CH_2-CH_2)-O$, with transition metal catalysis, preferably with Pd, Ni or Fe catalysis, to give a compound of the formula (VII'),

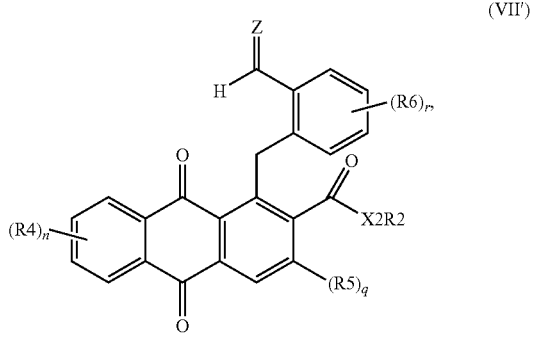
(VII')

and the compound (VII') is then, by a reaction with a suitable acid, hydrolyzed to give a compound (VIII), or alternatively, in a step (3.3), the compound (VI) is esterified with a compound of the formula (V) in which X2R2 is OH, to give a compound of the formula (VII"),

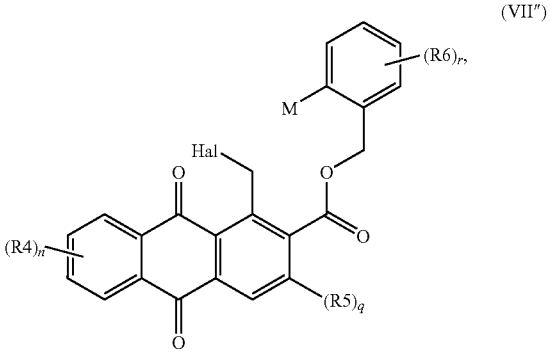
(VII")

and the compound (VII") is then, with transition metal catalysis, preferably with Pd, Ni or Fe catalysis, converted into a compound of the formula (VII'"),

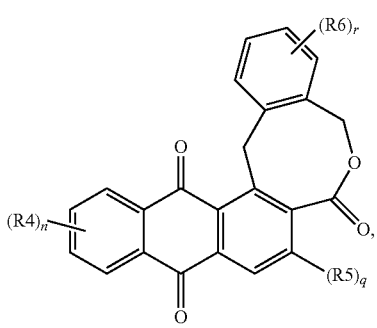
(VII'")

and the compound (VII'") is converted into a compound of the formula (VIII) by hydrolysis under basic or under acidic conditions, preferably under basic conditions, the benzyl alcohol formed is then oxidized to the aldehyde and the benzoic acid function formed is optionally esterified or amidated, in step (4) the compound (VIII) is reacted with a compound of the formula (IX)

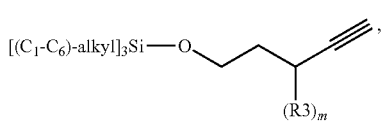

to give a compound of the formula (X),

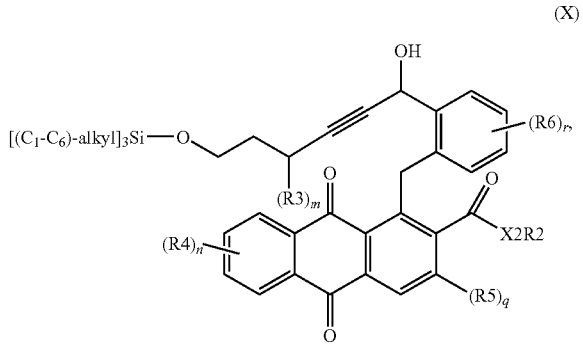

in step (5) the compound (X) is, with hydrogenation of the triple bond to a single bond and removal of the $[(C_1\text{-}C_6)\text{-alkyl}]_3\text{Si}$ group, converted into a compound of the formula (XI),

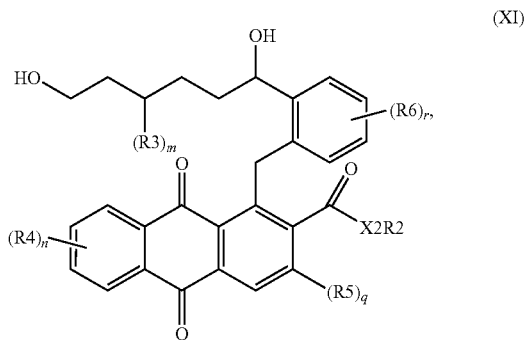

in step (6) the compound (XI) is oxidized to a compound of the formula (XII),

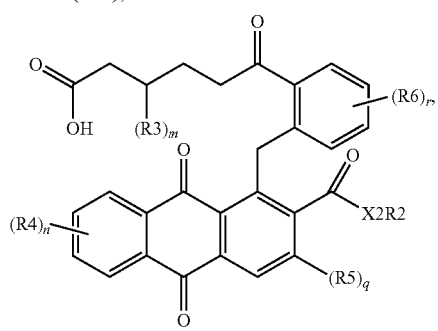

in step (7) the compound (XI) or the compound (XII) is oxidized to a compound of the formula (I) in which X1R1=OH, and in step (8) the compound obtained in step (7) is optionally converted into a compound of the formula (I) in which X1 is NH, N($C_1$-$C_6$)-alkyl or S and R1 is ($C_1$-$C_6$)-alkyl or benzyl, or a salt thereof.

DETAILED DESCRIPTION OF THE INVENTION

During the synthesis of compounds of the formula (I), the OH functions at R3, R4, R5 and/or R6, if present, are preferably temporarily provided with a suitable protective group, for example with a methyl, methoxymethyl, benzyl or p-methoxybenzyl group.

During the synthesis of the compounds of the formula (I), it may be necessary or desired to convert intermediate compounds containing C(O)X1R1 and/or C(O)X2R2 groups, if present in the compounds of the formulae (I), (IV), (V), (VII), (VIII), (VII'), (X), (XI) or (XII), into one another. This can be carried out by routes known per se to the person skilled in the art. For example, esters can be hydrolyzed under aqueous acidic or basic conditions to give the free acids. Using bases, the free carboxylic acids can then easily be converted into salts. Suitable bases are, for example, alkali metal hydroxides, such as NaOH or KOH. For preparing alternative carboxylic acid derivatives, it is furthermore possible to react esters or carboxylic acids after customary activation, for example with thionyl chloride, in the presence of a base with nucleophiles (for example $NH_2(C_1\text{-}C_6)$-alkyl, $NH_2$-benzyl, $NH[(C_1\text{-}C_6)\text{-alkyl}]_2$, $NH[(C_1\text{-}C_6)\text{-alkyl}][\text{benzyl}]$, $[(C_1\text{-}C_6)\text{-alkyl}]\text{-SH}$, benzyl-SH). Here, it is possible to react, if present, either both acid (derivative) functionalities together, to react selectively only one or to react both independently of one another in succession.

The term 'halogen' and 'Hal' means fluorine, chlorine, bromine or iodine, preferably chlorine or bromine.

The term '($C_1$-$C_6$)-alkyl' means a straight-chain or branched ($C_1$-$C_6$)-alkyl group which is optionally substituted by 1, 2, 3 or 4 substituents, where the substituents are selected from the group consisting of OH, ($C_1$-$C_4$)-alkyl, ($C_1$-$C_4$)-alkoxy, ($C_1$-$C_4$)-alkylthio, carbamoyl, carboxyl, trifluoromethyl, cyano, nitro, amino, ($C_1$-$C_4$)-alkylamino, di(($C_1$-$C_4$)-alkyl)amino, amidino, phenyl, O-phenyl, O-benzyl, NH-phenyl, NH-benzyl or halogen, -phenyl-($C_1$-$C_4$)-alkyl, -phenyl-O—($C_1$-$C_4$)-alkyl, preferably a ($C_1$-$C_4$)-alkyl group. '($C_1$-$C_6$)-alkyl' is, for example, methyl, ethyl, n-propyl, isopropyl, n-butyl, isobutyl, tert-butyl, methoxymethyl, benzyl or p-methoxybenzyl.

The term 'acyl' means —C(O)—($C_1$-$C_6$)-alkyl, for example acetyl or propanoyl; —C(O)—($C_6$-$C_{10}$)-aryl or —C(O)—($C_1$-$C_4$)-alkylene-($C_6$-$C_{10}$)-aryl, where ($C_6$-$C_{10}$)-aryl means an aromatic group which contains 6 to 10 carbon atoms, for example phenyl or tolyl; or —C(O)—($C_5$-$C_6$)-heteroaryl, where ($C_5$-$C_6$)-heteroaryl means a 5-6-membered ring having 1, 2, 3 or 4 heteroatoms, for example pyridyl, furyl, pyrrolyl, thienyl, thiazolyl or oxazolyl.

A salt of the compound of the formula (I) contains as cation for example an inorganic metal ion or an ammonium ion. The term 'cation' means in particular a pharmaceutically acceptable alkali metal or alkaline earth metal ion, for example sodium, potassium, calcium or magnesium, furthermore $NH_4^+$, a ($C_1$-$C_6$)-alkyl-alkylated ammonium ion, such as, for example, tetraethylammonium, diethanolammonium, morpholinonium or benzylammonium, or protonated forms of procaine, L-arginine or L-lysine.

A preferred compound of the formula (I) is a compound of the formula (I-A)

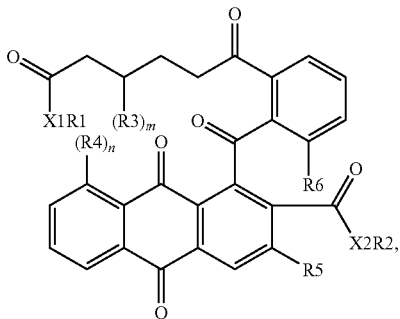

(I-A)

where R1 to R6, X1, X2, m and n independently of one another have the general or preferred meaning mentioned above.

Preferred definitions of the substituents of the compound of the formula (I) or of (I-A) are as follows:

R1 and R2 are preferably independently of one another H or $(C_1-C_6)$-alkyl, particularly preferably H or $(C_1-C_4)$-alkyl.
R2 is particularly preferably H.
R3 is preferably OH.
R4, R5 and R6 are preferably independently of one another OH or —O—$(C_1-C_6)$-alkyl.
X1 and X2 are preferably O.
m is preferably 0.
q is preferably 1.
r is preferably 1.

Special preference is given to a compound of the formula (I-A), in which
X1R1 is OH or O—$(C_1-C_6)$-alkyl,
X2R2 is OH,
R3 is OH,
R4 is OH or O—$(C_1-C_6)$-alkyl,
R5 is OH or O—$(C_1-C_6)$-alkyl,
R6 is OH or O—$(C_1-C_6)$-alkyl, and
m and n independently of one another are 0 or 1.

Step (1) consists of two experimentally separate partial reactions, a [4+2]-cycloaddition and a subsequent aromatization (via elimination). Preferably, X2R2 in the compound (III) is a group which can be eliminated later in sequence under mild conditions using, for example, TMS-OTf, for example O-tert-butyl. Compounds of type (II) can be prepared by processes known from the literature (Rapoport et al., J. Org. Chem. 1979, 44(13), 2153-2158; Cameron et al., Aust. J. Chem. 1981, 34, 1513-1522).

The [4+2]-cycloaddition step to give compounds of type (IV) is carried out by heating the components (II) and (III) for a period of 1 to 48 h, preferably 2-24 h, at a temperature of 80-180° C. without solvent or in a suitable inert solvent or in a mixture of inert solvents, for example in aliphatic, alicyclic or aromatic hydrocarbon, for example toluene, xylene or benzene. Step (1) is, if appropriate, carried out in the presence of a Lewis acid, for example $TiCl_4$, $Ti(i-Pr—O)_4$, $Ti(i-Pr—O)_2Cl_2$, $AlCl_3$ or $Sc(OTf)_3$. In principle, the reaction is accelerated by addition of Lewis acids, in which case it can also be carried out at lower reaction temperatures (<110° C.), where, however, side-reactions may occur in individual cases. If appropriate, step (1) can be carried out using a microwave reactor; also possible is the use of ionic liquids as reaction medium. If side-reactions do occur, these may be suppressed by using additives, for example organic or inorganic bases, proton sponges or free-radical scavengers, using, for example, alkali metal carbonates.

The aromatization of the primary [2+4]-cycloaddition product is then carried out by adding a suitable acid, for example silica gel, and stirring at 15-70° C. for 0.5 to 24 hours. Preferably, the solvent of the first partial step is replaced by water and a water-miscible organic solvent, for example THF. If the group R' is $(C_1-C_6)$-alkyl, it is generally not eliminated under the acidic aromatization conditions, resulting in the direct formation of compounds of type (IV) where R"=$(C_1-C_6)$-alkyl. If the group R' is $[(C_1-C_6)$-alkyl$]_3$silyl, it can be removed under the acid reaction conditions. Suitable for this purpose are dilute aqueous inorganic or organic acids, for example hydrochloric acid, sulfuric acid, acetic acid or p-toluene sulfonic acid. Particularly suitable is silica gel, which, if appropriate, is treated with one of these acids beforehand.

In step (2), initially the optional etherification or esterification of the OH group of (IV) is carried out by processes known per se to the person skilled in the art, for example by reaction with a $(C_1-C_6)$-alkyl halide, preferably methyl iodide, benzyl halide or an activated carboxylic acid derivative, for example an acyl chloride or anhydride, in the presence of an organic or inorganic base, for example potassium carbonate, in a suitable polar organic solvent, for example acetone, DMSO or DMF, at a temperature of 0-80° C. and reaction times of 0.5-12 h.

The further conversion into (V) is carried out by free-radical halogenation of the methyl group under photochemical and/or thermal reaction conditions known per se to the person skilled in the art, where in the latter case a free-radical initiator is used. Hal in the compound (V) is preferably bromine. The reaction is carried out, for example, by 5 to 24 hours of irradiation with light of a suitable spectral composition (for example sunlight or lamps with a relatively high UV fraction) of formula (IV) and N-bromosuccinimide in an inert solvent, for example a perhalogenated hydrocarbon, preferably carbon tetrachloride. Preferably, aliquots of a free-radical initiator, preferably dibenzoyl peroxide or azo-bis-isobutyronitrile (AIBN), are added at certain intervals (for example 15-180 min).

Step (3.1) is carried out by methods generally known per se to the person skilled in the art for transition metal-catalyzed cross coupling reactions (Nobre & Monteiro, Tetrahedron Lett. 2004, 45 8225-8228; Phopase et al., Tetrahedron Lett. 2004, 45, 6959-6962); for example, the compound (V) is reacted with an organometallic compound of type (VI) in which, if appropriate, the OH function is provided with a suitable protective group, in a temperature range of 0-150° C., preferably 5-40° C., and a reaction time of 1-72 h. Suitable protective groups are, for example, $[(C_1-C_6)$-alkyl$]_3$silyl], $(C_1-C_6)$-alkanoyl or acetal Z, where in the case of Z in the preparation of (VI') initially an oxidation is carried out by known methods, followed by acetalization. Preferably, the OH function is protected with a $[(C_1-C_6)$-alkyl$]_3$silyl] group, such as triethylsilyl, tri(isopropyl)silyl or a tert-butyldimethylsilyl group. If appropriate, the coupling reaction can be carried out in a microwave reactor, where the reaction temperature is in a range of 15-300° C. and the reaction time is from 1 minute to 120 minutes. Step (3.1) is carried out in one or more inert solvents, for example nonpolar aliphatic, alicyclic or aromatic hydrocarbons, such as, for example, toluene, xylene, benzene, compounds of weak polarity, such as, for example, THF or dibutyl ether, or polar compounds, such as, for example, NMP, DMF or DMSO, preferably THF and/or NMP, preferably under an atmosphere of inert gas.

In step (3.1), after the coupling reaction, the benzylic alcohol is oxidized using methods known per se to the person skilled in the art, for example by Dess-Martin oxidation using Dess-Martin periodinane in DCM as solvent, or preferably under the conditions of a Swern oxidation (reagents: DMSO, for example oxalyl chloride, triethylamine; inert solvent: DCM; temperature range: from −78° C. to 40° C.; reaction time: 1-24 h).

In step (3.2), the coupling step can be carried out analogously to step (3.1), where a compound of the formula (VI') is employed which contains a protected aldehyde function Z═O—($C_1$-$C_6$)-alkylene-O, preferably O—($CH_2$—$CH_2$)—O. After the coupling reaction, the protective group Z is treated in a suitable aqueous solvent, preferably a mixture of water and a polar organic solvent, for example acetone, at a temperature of 0-100° C., over a period of 0.5-48 h, with a suitable acid, for example PTS or, preferably, PPTS, where the acetal function is cleaved to the benzylic aldehyde.

In the alternative reaction step (3.3), the coupling step is carried out in an entropically favored intramolecular manner, where initially the coupling partners are esterified under conditions known per se with one another to give a compound of the formula (VII″), for example using a Mitsunobu-like esterification of (VI) with a compound (V) in which X2R2 is OH. Suitable for this purpose is a reagent combination consisting of an azodicarboxylic diester, for example diethylazodicarboxylate (DEAD) or diisopropyl azodicarboxylate (DIAD), and a phosphine, for example triphenylphosphine, tributylphosphine or diphenyl(2-pyridyl)phosphine. The reaction is carried out in an inert solvent (for example THF) in a temperature range of from −20° C. to 100° C. at reaction times of 1-24 h.

The hydrolysis of the compounds (VII‴) after the coupling is carried out under basic or under acidic conditions, preferably under basic conditions, with preference using aqueous NaOH or KOH solution. The benzyl alcohol formed in this manner is oxidized to the aldehyde by methods known per se to the person skilled in the art, for example by oxidizing via a Swern oxidation or a Dess-Martin periodinane oxidation. The benzoic acid function formed on the intermediate is esterified or amidated by methods known per se to the person skilled in the art by reacting, after activation of the benzoic acid function, for example with thionyl chloride, with the appropriate nucleophile (for example HO($C_1$-$C_6$)-alkyl, $NH_2$($C_1$-$C_6$)-alkyl, $NH_2$-benzyl, NH[($C_1$-$C_6$)-alkyl]$_2$, NH[($C_1$-$C_6$)-alkyl][benzyl], [($C_1$-$C_6$)-alkyl]-SH, benzyl-SH).

In steps (3.1), (3.2) and (3.3), preference is given to using a compound (VI) or (VI') where M═Sn(Bu)$_3$, whose preparation has been described by Meyer & Seebach (Chem. Ber. 1980, 113, 1304-1319).

In steps (3.1), (3.2) and (3.3), the coupling reaction is carried out in the presence of a suitable transition metal compound as catalyst or catalyst precursor, with Pd, Ni or Fe compounds being preferred, and where furthermore substoichiometric amounts are used. Suitable ligands for the transition metal compounds are, for example, alkylated or arylated phosphorus, nitrogen or arsenic compounds, and also N-heterocyclic carbenes, which may be mono- or bidentate ligands. Suitable ligands are, for example, P(Ph)$_3$, P(cyclohexyl)$_3$, P(2-furyl)$_3$, AsPh$_3$, dppe, dppp, dppf, dba, P(tert-bu)$_3$ or ibiox7, preferably AsPh$_3$ or dba. A preferred Pd catalyst is Pd$_2$(dba)$_3$. If appropriate, certain reaction-promoting additives, such as CsF, LiCl or copper (I)halides, preferably copper(I)iodide, may be added to the reaction mixture.

Step (4) is carried out by reacting the compound (VIII) at a temperature of from −78° C. to 25° C., preferably from −60° C. to −20° C., with an organometallic compound (IX'),

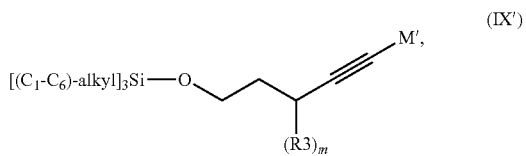

in which M' equals K, Na, Li, Ag, Cu, ZrCp$_2$Hal, CeCl$_2$, or Ti[O($C_1$-$C_6$)-alkyl]$_3$, preferably ZrCp$_2$Cl or Ti(i-Pr—O)$_3$, and which can be obtained from the compound (IX) by deprotonation, preferably using an organometallic compound (for example butyllithium), and subsequent reaction with the appropriate metal reagent, for example ZrCp$_2$Cl$_2$ or, preferably, ClTi(i-Pr—O)$_3$ in an inert solvent, preferably an ether, for example THF, and in a temperature range of from −30° C. to 20° C. over a period of 2-60 minutes.

In step (5), the compound (X) is hydrogenated under homogeneous catalysis or heterogeneous catalysis using methods known per se to the person skilled in the art, where the compound (X) or the desilylated compound (IX) vide infra is reacted under an atmosphere of hydrogen gas at pressures of from 1-50 bar at a reaction time of 15 minutes to 72 h and a temperature range of 15-80° C. in a suitable solvent in the presence of a catalyst which is preferably present in sub-stoichiometric amounts, preferably a finely divided transition metal, for example Pd, or a transition metal complex, for example Wilkinson catalyst. Suitable solvents are preferably polar aprotic solvents, for example ethyl acetate.

Step (5) furthermore comprises the removal of the terminal [($C_1$-$C_6$)-alkyl]$_3$Si group, exposing the terminal alcohol function of the compound (XI), by methods known per se to the person skilled in the art, where the compound (X) or the hydrogenated compound (IX) is reacted, for example, with a fluorine-containing reagent, for example TBAF or HF/pyridine, in a suitable solvent, for example a mixture of water and THF, over a period of from 30 minutes to 4 d and at a reaction temperature of from −40° C. to 70° C.

The partial steps of step (5) can be carried out in any order.

In step (6), the compound (XI) is oxidized by methods known per se to the person skilled in the art to give a compound (XII); this reaction can be carried out, for example, under the typical conditions of a "Jones oxidation" (mediated by Cr(VI)), where Jones reagent (chromium trioxide/sulfuric acid) is added to the compound (XI) in a suitable solvent, preferably a mixture of acetone and water, in a temperature range of from −40° C. to 60° C., and the mixture is stirred for a period of from 10 minutes to 24 h. Further suitable oxidation methods are the reaction with potassium permanganate, if appropriate catalyzed by a Lewis acid (Lai & Lee, Tetrahedron 2002, 58, 9879), the treatment with a Ru(III) salt/metal periodate mixture or a treatment with an RuCl$_3$/$^t$BuOOH mixture.

In step (7), the compound (XI) or the compound (XII) is converted into a compound of the formula (I), for example by reaction with potassium permanganate, if appropriate catalyzed by a Lewis acid, or oxidation using a trifluorinated 1,1-dimethyldioxirane, or by using molecular oxygen in the presence of a catalyst, for example activated carbon (Kawabata & Hayashi, *Tetrahedron Lett.* 2004, 58, 5457), or, preferably, by treatment with an Ru(III) salt/metal periodate mixture, treatment with an RuCl$_3$/$^t$BuOOH mixture or oxidation using TEMPO, or particularly preferably using Br$_2$ in a mixture of CCl$_4$ and water under irradiation with light, for example using a tungsten lamp at a temperature of 0-70° C. according to Krohn et al. (Tetrahedron 2006, 62, 1223-1230).

In step (8), the compound obtained in step (7) is, under conditions known per se to the person skilled in the art, if appropriate either converted into a salt by reaction with a suitable base, for example with NaOH or KOH, or the acid function formed on the intermediate is, by methods known per se to the person skilled in the art, esterified or amidated by reacting with the appropriate nucleophile (NH$_2$(C$_1$-C$_6$)-alkyl, NH$_2$-benzyl, NH[(C$_1$-C$_6$)-alkyl]$_2$, NH[(C$_1$-C$_6$)-alkyl][benzyl], [(C$_1$-C$_6$)-alkyl]-SH, benzyl-SH) following activation of the acid function, for example with thionyl chloride.

The present invention furthermore relates to intermediates in the process described above for preparing mumbaistatin derivatives of the formula (I), in particular to the intermediates of the formulae (IV), (V), (VII), (VII'), (VII''), (VII'''), (VIII), (IX), (X), (XI) and (XII), where preference is given to compounds of the formulae (VII), (VII'), (VII''), (VII'''), (VIII), (IX), (X), (XI) and (XII) which carry the R6 substituent ortho to the benzophenone methylene bridge. Hereinbelow, these compounds are referred to as (VII-A), (VII'-A), (VII''-A), (VII'''-A), (VIII-A), (IX-A), (X-A), (XI-A) and (XII-A), the compound (XII-A), for example, has the formula

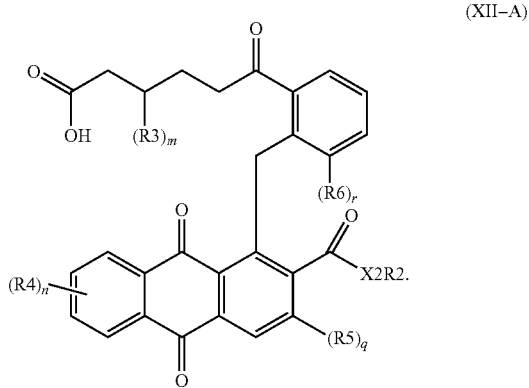

(XII-A)

Particular preference is given to a compound of the formula (IV), where X2R2 is OH or O—(C$_1$-C$_6$)-alkyl, R4 is OH or O—(C$_1$-C$_6$)-alkyl, and n and q independently of one another are 0 or 1. Particular preference is given to a compound (IV) in which X2R2 is OH or O—(C$_1$-C$_6$)-alkyl, R4 is OH or O—(C$_1$-C$_6$)-alkyl, n is 0 or 1, and q is 1.

Particular preference is given to a compound of the formula (V) where X2 is O, R2 is H or (C$_1$-C$_6$)-alkyl, R4 and R5 independently of one another are OH or O—(C$_1$-C$_6$)-alkyl, n and q independently of one another are 0 or 1, and Hal is chlorine or bromine. Particular preference is given to a compound of the formula (V) in which X2 is O, R2 is H or (C$_1$-C$_6$)-alkyl, R4 and R5 are O—(C$_1$-C$_6$)-alkyl, n is 0 or 1, q is 1, and Hal is bromine.

Particular preference is given to a compound of the formula (VII) or (VII-A), where X2 is O, R2 is H or (C$_1$-C$_6$)-alkyl, R4, R5 and R6 independently of one another are OH or O—(C$_1$-C$_6$)-alkyl, and n, q and r independently of one another are 0 or 1. Particular preference is given to a compound (VII) in which X2 is O, R2 is H or (C$_1$-C$_6$)-alkyl, R4, R5 and R6 are O—(C$_1$-C$_6$)-alkyl, n is 0 or 1, and q and r are 1.

Particular preference is given to a compound of the formula (VII') or (VII'-A), where X2R2 is OH or O—(C$_1$-C$_6$)-alkyl, and furthermore R4, R5 and R6 independently of one another are OH or O—(C$_1$-C$_6$)-alkyl, and n, q and r independently of one another are 0 or 1. Especially preferably, X2R2 is OH, furthermore R4, R5 and R6 are O—(C$_1$-C$_6$)-alkyl, n is 0 or 1, and q and r are 1. Z is preferably O—(CH$_2$—CH$_2$)—O.

Particular preference is given to a compound of the formula (VII'') or (VII''-A), where R4, R5 and R6 independently of one another are OH or O—(C$_1$-C$_6$)-alkyl, Hal is chlorine, bromine or iodine, and n, q and r independently of one another are 0 or 1. Especially preferably, R4, R5 and R6 are O—(C$_1$-C$_6$)-alkyl, Hal is chlorine or bromine, n is 0 or 1, and q and r are 1.

Particular preference is given to a compound of the formula (VII''') or (VII'''-A), where R4, R5 and R6 independently of one another are OH or O—(C$_1$-C$_6$)-alkyl, and n, q and r independently of one another are 0 or 1. Especially preferably, R4, R5 and R6 are O—(C$_1$-C$_6$)-alkyl, n is 0 or 1, and q and r are 1.

Particular preference is furthermore given to a compound (VIII) or (VIII-A), where X2 is O, R2 is H or (C$_1$-C$_6$)-alkyl, R4, R5 and R6 independently of one another are OH or O—(C$_1$-C$_6$)-alkyl, and n, q and r independently of one another are 0 or 1. Particular preference is given to a compound (VIII) in which X2 is O, R2 is H or (C$_1$-C$_6$)-alkyl, R4, R5 and R6 are O—(C$_1$-C$_6$)-alkyl, n is 0 or 1, and q and r are 1.

The compound of the formula (IX) can be used in racemic form or as an enantiomer, for example as the (R)- or as the (S)-form.

Particular preference is given to a compound of the formula (XI) or (XI) in which X2R2 is OH or O—(C$_1$-C$_6$)-alkyl, R4, R5 and R6 independently of one another are OH or O—(C$_1$-C$_6$)-alkyl, and n, q and r independently of one another are 0 or 1.

Particular preference is given to a compound of the formula (XII) or (XII-A) where X2R2 is OH or O—(C$_1$-C$_6$)-alkyl, R4, R5 and R6 independently of one another are OH or O—(C$_1$-C$_6$)-alkyl, and n, q and r independently of one another are 0 or 1.

Using the present process, it is possible to obtain mumbaistatin derivatives in a 7- to 8-step synthesis starting with the compound (II). The synthesis route described is distinguished by improved efficiency and yield in the synthesis of the highly substituted anthraquinone building block of the compound of the formula (I) via a Diels-Alder cycloaddition, without complicated protective group manipulations being required. Furthermore, for the first time, the use of a transition metal-catalyzed reaction offers access to tetra-ortho-substituted benzophenones in combination with an anthraquinone skeleton in the mumbaistatin derivatives (I) and their intermediates.

Abbreviations:

| | |
|---|---|
| Ac | acetyl |
| Bu | butyl |
| dba | dibenzylidene acetone |
| DCM | dichloromethane |
| dppe | 1,2-bis(diphenylphosphino)ethane |
| dppf | 1,1'-bis(diphenylphosphino)ferrocene |
| dppp | 1,3-bis(diphenylphosphino)propane |
| EA | ethyl acetate |
| eq. | equivalent |
| MOM | methoxymethyl |
| m.p. | melting point |
| Ms | mesyl |
| MTBE | methyl tert-butyl ether |
| MW | molecular weight |
| PTS | para-toluenesulfonic acid |

| | | |
|---|---|---|
| PPTS | pyridinium para-toluenesulfonate | |
| $R_f$ | retention factor | |
| TBAF | tetrabutylammonium fluoride | |
| TBS | tert-butyldimethylsilyl | |
| Tf | trifluoromethanesulfonyl | |
| THF | tetrahydrofuran | |
| TLC | thin-layer chromatogram | |
| TMS | trimethylsilyl | |
| Ts | tosyl | |

The reaction steps mentioned above and the reactions described below are carried out exposed to air or under protective gas, preferably under protective gas.

EXAMPLES

Example 1

Preparation of tert-butyl 3-trimethylsilanyloxy-2-(1-trimethylsilanyloxyvinyl)but-2-enoate

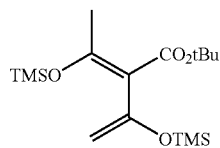

34.2 ml (0.21 mol) of tert-butyl 3-oxobutanoate were dissolved in 300 ml of dichloromethane, and 20 g (0.21 mol, 1.0 eq.) of anhydrous magnesium chloride were added. At 0° C., 33.9 ml (0.42 mol, 2.0 eq.) of dry pyridine were added to the suspension, which was stirred vigorously. After 15 minutes, 14.3 ml (0.21 mol, 1.0 eq.) of acetyl chloride were added dropwise, and the mixture was stirred at RT for 1 hour. At 0° C., excess pyridine was neutralized with dilute hydrochloric acid (37 ml of conc. hydrochloric acid and 100 ml of water), and the organic phase was separated off. The aqueous phase was extracted with MTBE (3×100 ml), and the combined organic phases were washed with saturated NaCl solution and dried over $MgSO_4$. Removal of the solvent gave 41.2 g (0.206 mol, 98%) of tert-butyl 2-acetyl-3-oxobutanoate in the form of a pale yellow oil.

Without further purification, 40.2 g (0.20 mol) of the tert-butyl 2-acetyl-3-oxobutanoate obtained in this manner in 50 ml of toluene were mixed with 107.0 ml (0.44 mol, 2.2 eq.) of BSA, and the mixture was stirred at RT for 2 d. After removal of the solvent on a rotary evaporator, the product was subjected to vacuum distillation (0.36 mbar, 75° C.), which gave 60.6 g (0.176 mol, 88%) of the desired tert-butyl 3-trimethylsilanyloxy-2-(1-trimethylsilanyloxyvinyl)but-2-enoate as a yellowish oil. In a further experiment, yields of 97 and 84% were obtained.

$C_{16}H_{32}O_4Si_2$, MW 344.59 g/mol; TLC (hexane/ethyl acetate 1:1): $R_f$=0.71.

Example 2

Preparation of tert-butyl 3-hydroxy-1-methyl-9,10-dioxo-9,10-dihydroanthracene-2-carboxylate

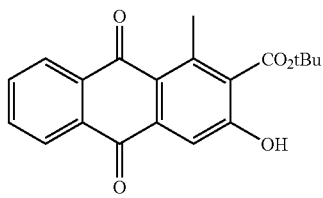

27.9 g (81.2 mmol, 2.0 eq.) of tert-butyl 3-trimethylsilanyloxy-2-(1-trimethylsilanyloxyvinyl)but-2-enoate (Example 1) and 7.8 g (40.6 mmol) of 2-chloro-1,4-naphthoquinone (Gupta & Franck, Synlett 1990, 355-357) were dissolved in 325 ml of anhydrous toluene and heated at reflux for 24 hours. The solvent was then removed on a rotary evaporator, and 250 ml of THF were added to the brown oily residue. After addition of 10 ml of water, the mixture was stirred at RT for 1 d. About 50 ml of silica gel were then added whereupon the temperature of the mixture increased, and the solvent was then removed. The crude product, absorbed on the silica gel, was then filled into a frit filled with silica gel and eluted with DCM as solvent. The yellow product band was collected separately, giving, after removal of the solvent, 7.7 g (22.8 mmol, 55%) of tert-butyl 3-hydroxy-1-methyl-9,10-dioxo-9, 10-dihydroanthracene-2-carboxylate which still contained small amounts of impurities; however, these could be removed completely in the next synthesis step. In a further experiment, a yield of 48% was obtained.

$C_{20}H_{18}O_5$, MW 338.35 g/mol; TLC (DCM): $R_f$=0.14.

$^1$H-NMR (300 MHz; $CDCl_3$): δ [ppm]=1.65 (s, 9H, —$OCMe_3$); 2.93 (s, 3H, -Me at C-1); 7.20-8.20 (m, 4H, H-5, H-6, H-7, H-8); 7.75 (s, 1H, H-4); 10.51 (s, 1H, OH).

$^{13}$C-NMR (75 MHz; $CDCl_3$): δ [ppm]=21.6 (q, Me at C-1); 28.3 (q, —$OCMe_3$); 83.0 (s, —$OCMe_3$); 113.9 (d, C-4); 121.8 (s, C-2); 129.8 (d, C-5, C-8); 131.9 (d, C-6, C-7); 132.6 (s, C-9a); 139.4 (s, C-10a, C-8a); 141.6 (s, C-1); 145.0 (s, C-4a); 161.8 (s, C-3); 167.0 (s, C=O at C-2); 183.3 (s, C-9, C-10).

Example 3

Preparation of tert-butyl 3,8-dihydroxy-1-methyl-9,10-dioxo-9,10-dihydroanthracene-2-carboxylate

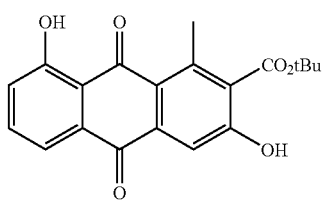

20.1 g (58.5 mmol, 2.0 eq.) of tert-butyl 3-trimethylsilanyloxy-2-(1-trimethylsilanyloxyvinyl)but-2-enate and 5.05 g (24.3 mmol) of 2-chloro-8-hydroxy-1,4-naphthoquinone (Giles & Roos, J. Chem. Soc Perkin 11976, 2057-2060) were dissolved in 125 ml of anhydrous toluene and heated at reflux for 24 hours. The solvent was then removed on a rotary evaporator, and 150 ml of THF were added to the brown oily residue. After the addition of 10 ml of water, the mixture was stirred at RT for 1d. About 50 ml of silica gel were then added, and the mixture was freed from the solvent. The crude product, absorbed on the silica gel, was then filled into a frit filled with silica gel and eluted using DCM as mobile phase. The product band, which has an intensive yellow color and is easy to isolate, was collected separately, and, after removal of the solvent, it was possible to isolate 3.8 g (10.9 mmol, 45%) of the brown tert-butyl 3,8-dihydroxy-1-methyl-9,10-dioxo-9,10-dihydroanthracene-2-carboxylate which still contained small amounts of impurities; however, these could be removed completely in the next synthesis step.

$C_{20}H_{18}O_6$, MW 354.35 g/mol; m.p.: 207° C.; TLC (DCM): $R_f$=0.11.

$^1$H-NMR (300 MHz; CDCl$_3$): δ [ppm]=1.65 (s, 9H, —OCMe$_3$); 2.94 (s, 3H, Me at C-1); 7.28 (dd, 1H, H7); 7.59 (t, 1H, H-6); 7.73 (s, 1H, H-4); 7.74 (dd, 1H, H-5); 10.22 (s, 1H, —OH at C-3); 12.88 (s, 1H, —OH at C-8).

$^{13}$C-NMR (75 MHz; CbCl$_3$): δ [ppm]=21.3 (q, Me at C-1); 28.0 (q, —OCMe$_3$); 83.2 (s, —OCMe$_3$); 113.9 (d, C-4); 119.1 (d, C-7); 122.0 (s, C-2); 122.4 (d, C-5); 126.6 (s, C-8a); 132.6 (s, C-9a); 133.3 (d, C-6); 140.8 (s, C-10a); 141.6 (s, C-1); 145.0 (s, C-4a); 158.6 (s, C-8); 161.8 (s, C-3); 167.0 (s, C=O at C-2); 183.0 (s, C-9, C-10).

Example 4

Preparation of tert-butyl 3-methoxy-1-methyl-9,10-dioxo-9,10-dihydroanthracene-2-carboxylate

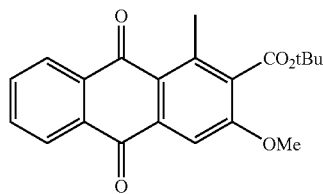

2.88 g (20.8 mmol, 2.0 eq.) of anhydrous K$_2$CO$_3$ and 5.2 ml (83.2 mmol, 8.0 eq.) of methyl iodide were added to 3.5 g (10.4 mmol) of tert-butyl 3-hydroxy-1-methyl-9,10-dioxo-9,10-dihydroanthracene-2-carboxylate in 70 ml of acetone, and the mixture was heated at reflux for 3 hours. After cooling, the acetone was distilled off on a rotary evaporator. The mixture that remained was taken up in DCM and extracted with water. Drying over MgSO$_4$, washing with saturated NaCl solution and removal of the solvent gave 3.49 g (9.9 mmol, 95%) of the methylated product tert-butyl 3-methoxy-1-methyl-9,10-dioxo-9,10-dihydroanthracene-2-carboxylate in analytically pure form as a brownish solid. In a further experiment, a yield of 92% was obtained.

$C_{21}H_{20}O_5$, MW 352.38 g/mol; m.p.: 158° C.; TLC (DCM): $R_f$=0.21.

$^1$H-NMR (300 MHz; CDCl$_3$): δ [ppm]=1.60 (s, 9H, —OCMe$_3$); 2.76 (s, 3H, -Me at C-1) 4.00 (s, —OMe); 7.6-7.8 (m, 2H, H-6, H-7); 8.20-8.3 (m, 2H, H-5, H-8); 7.75 (s, 1H, H-4).

$^{13}$C-NMR (75 MHz; CDCl$_3$): δ [ppm]=19.2 (q, Me at C-1); 28.2 (q, —OCMe$_3$); 56.4 (q, —OMe); 83.1 (s, —OCMe$_3$); 107.3 (d, C-4); 126.1 (s, C-2); 126.6/127.2 (s, C-5, C-8); 132.4 (s, C-9a); 133.2/134.3 (d, C-6, C-7); 135.0 (s, C-5a, C-10a); 136.9 (s, C-1); 140.4 (s, C-4a); 159.3 (s, C-3); 166.3 (s, C=O at C-2); 183.2/183.7 (s, C-9, C-10).

Example 5

Preparation of tert-butyl 3,8-dimethoxy-1-methyl-9,10-dioxo-9,10-dihydroanthracene-2-carboxylate

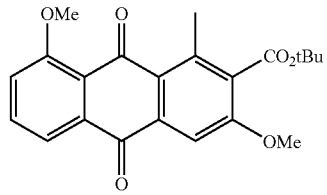

2.92 g (20.8 mmol, 4.0 eq.) of anhydrous K$_2$CO$_3$ and 5.26 ml (84.5 mmol, 16.0 eq.) of methyl iodide were added to 1.87 g (5.28 mmol) of tert-butyl 3,8-dihydroxy-1-methyl-9,10-dioxo-9,10-dihydroanthracene-2-carboxylate in 40 ml of acetone, and the mixture was heated at reflux for 8 hours. After cooling, the acetone was distilled off on a rotary evaporator. The mixture that remained was taken up in DCM and extracted with water. After washing with saturated NaCl solution and drying over MgSO$_4$, the mixture was filtered through a silica plug and the solvent was removed. This gave 1.92 g (5.02 mmol, 95%) of the methylated product tert-butyl 3,8-dimethoxy-1-methyl-9,10-dioxo-9,10-dihydroanthracene-2-carboxylate in analytically pure form as an ocher-colored solid.

$C_{22}H_{22}O_6$, MW 382.41 g/mol; TLC (DCM): $R_f$=0.25.

$^1$H-NMR (300 MHz; CDCl$_3$): δ [ppm]=1.59 (s, 9H, —OCMe$_3$); 2.70 (s, 3H, -Me at C-1); 3.96 (s, 3H, —OMe at C-3); 4.00 (s, 3H, —OMe at C-8); 7.30 (d, 1H, H-7); 7.61 (s, 1H, H-4); 7.62 (t, 1H, H-6); 7.83 (d, 1H, H-5).

$^{13}$C-NMR (75 MHz; CDCl$_3$): δ [ppm]=18.8 (q, Me at C-1); 28.1 (q, —OCMe$_3$); 56.3 (q, —OMe at C-3); 56.6 (q, —OMe at C-8); 83.0 (s, —OCMe$_3$); 106.3 (d, C-4); 118.2 (d, C-7); 126.0 (s, C-2); 122.1 (d, C-5); 125.1 (s, C-8a); 132.1 (s, C-9a); 134.0 (d, C-6); 134.7 (s, C-10a); 135.5 (s, C-1); 139.3 (s, C-4a); 158.5 (s, C-8); 159.7 (s, C-3); 167.0 (s, C=O at C-2); 183.4 (s, C-9, C-10).

Example 6

Preparation of tert-butyl 1-bromomethyl-3-methoxy-9,10-dioxo-9,10-dihydroanthracene-2-carboxylate

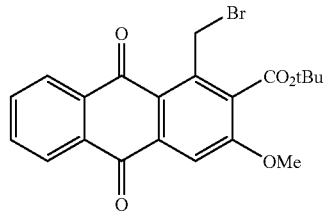

3.49 g (9.9 mmol) of tert-butyl 3-methoxy-1-methyl-9,10-dioxo-9,10-dihydroanthracene-2-carboxylate were dissolved in 370 ml of dry and degassed CCl$_4$, and 2.29 g (12.9 mmol, 1.3 eq.) of NBS were added. The solution was heated at reflux and, under irradiation with light (150 W lamp, high UV fraction) capped at this temperature for 2×8 hours. During this time, every 3 hours, in 5 portions, in each case 72 mg (0.297 mmol, 3 mol %) of dibenzoyl peroxide (in each case dissolved in 1 ml of $CCl_4$) were added as free-radical initiator. After the reaction mixture had cooled, the insoluble succinimide was filtered off and the solvent was removed. This gave 4.23 g (9.8 mmol, 99%) of the benzylically brominated anthraquinone tert-butyl 1-bromomethyl-3-methoxy-9,10-dioxo-9,10-dihydroanthracene-2-carboxylate analytically pure in the form of a yellowish-brown solid. In a further experiment, a yield of 92% was obtained.

$C_{21}H_{19}BrO_5$, MW 431.28 g/mol; TLC (cyclohexane/EA 2:1): $R_f$=0.45; m.p.: 153° C.

$^1$H-NMR (300 MHz; $CDCl_3$): δ [ppm]=1.66 (s, 9H, —$OCMe_3$); 3.73 (s, 3H, —OMe); 5.15 (s, 2H, —$CH_2Br$); 7.23 (s, 1H, H-4); 7.60-8.35 (m, 4H, H-5, H-6, H-7, H-8).

$^{13}$C-NMR (75 MHz; $CDCl_3$): δ [ppm]=27.5 (t, C-11); 28.2 (q, —$OCMe_3$); 56.5 (q, —OMe); 83.3 (s, —$OCMe_3$); 107.2 (d, C-4); 126.2 (s, C-2); 126.6 (d, C-5); 127.3 (d, C-8); 132.4 (s, C-9a); 133.6 (d, C-6); 134.5 (d, C-7); 135.1 (s, C-5a, C-8a); 136.9 (s, C-1); 140.0 (s, C-4a); 159.3 (s, C-3); 166.4 (s, C=O at C-2); 183.2/183.6 (s, C-9, C-10).

Example 7

Preparation of tert-butyl 1-bromomethyl-3,8-dimethoxy-9,10-dioxo-9,10-dihydroanthracene-2-carboxylate

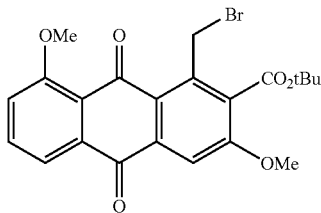

1.9 g (4.97 mmol) of tert-butyl 3,8-dimethoxy-1-methyl-9,10-dioxo-9,10-dihydroanthracene-2-carboxylate were dissolved in 110 ml of dry and degassed $CCl_4$, and 1.15 g (6.46 mmol, 1.3 eq.) of NBS were added. The solution was heated at reflux and, under irradiation with light (150 W lamp, high UV fraction), kept at this temperature for 2 times 8 hours. During this time, every 3 hours, in 5 portions, in each case 36 mg (0.15 mmol, 3 mol %) of dibenzoyl peroxide (in each case dissolved in 1 ml of $CCl_4$) were added as free-radical initiator. After the reaction mixture had cooled, the insoluble succinimide was filtered off and the solvent was removed. The reaction mixture was purified by column chromatography. This gave 1.54 g (3.33 mmol, 67%) of the benzylically brominated anthraquinone tert-butyl 1-bromomethyl-3,8-dimethoxy-9,10-dioxo-9,10-dihydroanthracene-2-carboxylate in the form of a reddish-yellow solid.

$C_{22}H_{21}BrO_6$, MW 461.30 g/mol; TLC (cyclohexane/EA 2:1): $R_f$=0.32; m.p.: 164° C.

$^1$H-NMR (300 MHz; $CDCl_3$): δ [ppm]=1.63 (s, 9H, —$OCMe_3$); 3.98 (s, 3H, —OMe at C-3); 4.01 (s, 3H, —OMe at C-8); 5.13 (s, 2H, —$CH_2Br$); 7.34 (d, 1H. H-7); 7.64 (t, 1H, H-6); 7.72 (s, 1H, H-4); 7.85 (d, 1H, H-5).

$^{13}$C-NMR (75 MHz; $CDCl_3$): δ [ppm]=26.2 (t, C-11); 28.5 (q, —$OCMe_3$); 56.4 (q, —OMe); 84.0 (s, —$OCMe_3$); 107.4 (d, C-4); 118.0 (d, C-7); 125.1 (s, C-8a); 126.3 (s, C-2); 126.6 (d, C-5); 163.3 (s, C-8); 132.0 (s, C-9a); 133.1 (d, C-6); 134.7 (s, C-10a); 137.2 (s, C-1); 140.0 (s, C-4a); 159.0 (s, C-3); 165.7 (s, C=O at C-2); 183.5 (s, C-9, C-10).

Example 8

Preparation of 3-methoxy-2-(tributylstannyl)benzyl Alcohol

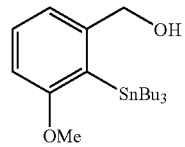

2.00 g (14.5 mmol) of 3-methoxybenzyl alcohol were dissolved in 40 ml of dry benzene. At 0° C., 19.91 ml (31.9 mmol, 2.2 eq.) of a 1.6 molar n-BuLi solution were slowly added dropwise, where the white suspension formed after addition of one equivalent of n-BuLi changed its color to dark red during the addition of the second equivalent. Stirring at RT was continued for another 2 hours, and 5.1 ml (18.8 mmol, 1.3 eq.) of tributyltin chloride were then added at 0° C. The mixture was stirred at RT overnight, and 40 ml of saturated $NH_4Cl$ solution were then added and the mixture was extracted three times with 70 ml of EA. After washing of the organic phase with saturated NaCl solution and drying over $MgSO_4$, the solvent was removed. The crude product was purified by column chromatography (reversed-phase silica RP-18, MeCN), which gave 4.83 g (11.3 mmol, 78%) of 3-methoxy-2-(tributylstannyl)benzyl alcohol as a colorless oil. In a further experiment, a yield of 60% was obtained.

$C_{20}H_{36}O_2Sn$, MW 427.21 g/mol; TLC (RP-18, MeCN): $R_f$=0.68.

$^1$H-NMR (300 MHz; $CDCl_3$): δ [ppm]=0.83 (t, 9H, butyl-H-4); 1.00-1.10 (m, 6H, butyl-H-1); 1.20-1.39 (m, 6H, butyl-H-2); 1.40-1.61 (m, 6H, butyl-H-3); 3.75 (s, 3H, —OMe); 4.55 (d, 2H, —$CH_2OH$); 6.73 (d, 1H, H-4); 7.15 (d, 1H, H-6); 7.29 (t, 1H, H-5).

$^{13}$C-NMR (75 MHz; $CDCl_3$): δ [ppm]=12.3 (t, butyl-C-1); 13.7 (q, butyl-C-4); 27.5 (t, butyl-C-3); 29.2 (t, butyl-C-2); 56.2 (q, —OMe); 67.1 (t, —$CH_2OH$); 112.6 (d, C-4); 119.8 (d, C-6); 126.5 (s, C-2); 130.4 (d, C-5); 149.0 (s, C-1); 170.2 (s, C-3).

Example

Preparation of tert-butyl 1-(2'-hydroxymethyl-6'-methoxybenzyl)-3-methoxy-9,10-dioxo-9,10-dihydroanthracene-2-carboxylate

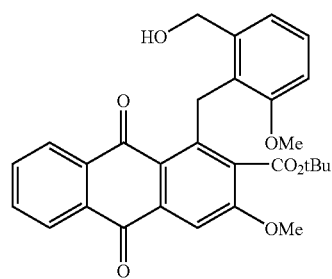

In a Schlenk tube with reflux condenser, 100 mg (232 μmol) of tert-butyl 1-bromomethyl-3-methoxy-9,10-dioxo-9,10-dihydroanthracene-2-carboxylate were dissolved in a mixture of 2.0 ml of THF and 2.0 ml of NMP. 3.5 mg (20 μmol, 8 mol %) of copper(I) iodide, 11.6 mg (37 μmol, 16 mol %) of triphenylarsine and 8.9 mg (9 μmol, 4 mol %) of $Pd_2(dba)_3$ were then added with stirring. Twice, the brown-red solution was degassed under reduced pressure and saturated with argon. 119 mg (278 μmol, 1.2 eq.) of 3-methoxy-2-(tributylstannyl)benzyl alcohol were then injected through the tube. The reaction mixture was heated at a temperature of 80° C. for 20 hours, during which time the color of the solution slowly changed from brown to black. After cooling, 15 ml of $H_2O$ were added, and the mixture was extracted with 3×50 ml of EA. Drying over $MgSO_4$ and removal of the solvent gave a brown slimy solid which was purified by column chromatography (cyclohexane/EA 2:1). This gave 49.8 mg (100 μmol, 43%) of the Stille coupling product tert-butyl 1-(2'-hydroxymethyl-6'-methoxybenzyl)-3-methoxy-9,10-dioxo-9,10-dihydroanthracene-2-carboxylate in the form of a yellow solid. In a further experiment, a yield of 17% was obtained.

$C_{29}H_{28}O_7$, MW 488.53 g/mol; TLC (cyclohexane/EA 2:1): $R_f$=0.26; m.p.: 173° C.

$^1$H-NMR (300 MHz; $CDCl_3$): δ [ppm]=1.38 (s, 9H, —$OCMe_3$); 3.41 (s, 3H, —OMe at C-3); 4.00 (s, 3H, —OMe at C-6'); 4.64 (s, 2H, $CH_2$ at C-1'); 4.65 (d, 2H, —$CH_2OH$); 6.63 (d, 1H, H-5'); 7.03 (d, 1H, H-3'); 7.15 (t, 1H, H-4'); 7.60-7.75 (m, 2H, H-6, H-7); 7.76 (s, 1H, H-4); 7.95-8.05 (m, 1H, H-5); 8.10-8.20 (m, 1H, H-8).

$^{13}$C-NMR (75 MHz; $CDCl_3$): δ [ppm]=12.0 (t, C-11); 29.0 (q, —$OCMe_3$); 56.0 (q, —OMe at C-3); 56.5 (q, —OMe at C-6'); 62.6 (t, HO—$CH_2$— at C-2'); 74.8 (s, —$OCMe_3$); 112.8 (d, C-4); 113.5 (d, C-5'); 119.6 (s, C-2); 120.1 (d, C-3'); 127.0 (d, C-4'); 127.3 (s, C-1'); 129.3 (d, C-5), 129.8 (d, C-8); 131.8 (s, C-9a); 133.9 (d, C-6); 134.5 (d, C-7); 136.4 (s, C-5a, C-8a); 140.0 (s, C-4a); 141.5 (s, C-1); 142.0 (s, C-2'); 162.4 (s, C-6'); 166.4 (s, C=O at C-2); 167.3 (s, C-3); 183.3/183.8 (s, C-9, C-10).

Example 10

Preparation of tert-butyl 1-(2'-formyl-6'-methoxy-benzyl)-3-methoxy-9,10-dioxo-9,10-dihydroanthracene-2-carboxylate

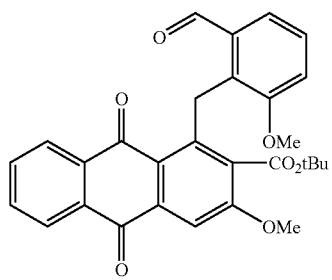

100 mg (204 μmol) of tert-butyl 1-(2'-hydroxymethyl-6'-methoxybenzyl)-3-methoxy-9,10-dioxo-9,10-dihydroanthracene-2-carboxylate were dissolved in 6 ml of DCM and cooled to −78° C. 290 μl (4.0 mmol, 20 eq.) of DMSO (dried over 4 Å molecular sieve) and, after 5 minutes, 172 μl (2.0 mmol, 10 eq.) of oxalyl chloride were then added. After a further 60 minutes, 1.42 ml (10.2 mmol, 50 eq.) of triethylamine (anhydrous) were added, and the reaction mixture was slowly warmed to room temperature overnight. After the addition of 20 ml of $H_2O$, the phases were separated and the aqueous phase was extracted with 3×30 ml of EA. The organic phase was washed with saturated NaCl solution and dried over $MgSO_4$, and the solvent was then removed. Without further purification, 97 mg (200 μmol, 98%) of the free aldehyde tert-butyl 1-(2'-formyl-6'-methoxybenzyl)-3-methoxy-9,10-dioxo-9,10-dihydroanthracene-2-carboxylate were obtained in pure form in the form of a bright yellow solid.

$C_{29}H_{26}O_7$, MW 486.51 g/mol; TLC (cyclohexane/EA 2:1): $R_f$=0.37; m.p.: 187° C.

$^1$H-NMR (300 MHz; $CDCl_3$): δ[ppm]=1.42 (s, 9H, —$OCMe_3$); 3.54 (s, 3H, —OMe at C-3); 4.02 (s, 3H, —OMe at C-6'); 4.96 (s, 2H, $CH_2$ at C-1'); 6.95 (d, 1H, H-5'); 7.23 (t, 1H, H-4'); 7.43 (d, 1H, H-3'); 7.60-7.80 (m, 2H, H-6, H-7); 7.78 (s, 1H, H-4); 7.92-8.05 (m, 1H, H-5); 8.15-8.22 (m, 1H, H-8); 10.33 (s, 1H, —CHO).

$^{13}$C-NMR (75 MHz; $CDCl_3$): δ [ppm]=11.6 (t, C-11); 29.1 (q, —$OCMe_3$); 56.0 (q, —OMe at C-3); 56.2 (q, —OMe at C-6'); 72.8 (s, —$OCMe_3$); 112.8 (d, C-4); 119.4 (s, C-2); 120.4 (d, C-5'); 122.6 (d, C-3'); 127.4 (d, C-4'); 129.6 (s, C-1'); 129.6 (d, C-5); 129.9 (d, C-8); 131.5 (s, C-9a); 132.2 (d, C-6); 133.0 (d, C-7); 137.9 (s, C-2'); 139.1 (s, C-5a, C-8a); 145.3 (s, C-4a); 146.5 (s, C-1); 162.5 (s, C-6'); 167.0 (s, C=O at C-2); 167.2 (s, C-3); 183.5/183.8 (s, C-9, C-10); 190.4 (d, —CHO).

Example

Preparation of 5-(tert-butyldimethylsiloxy)pent-1-yne

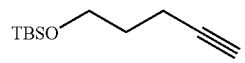

5.00 g (59.4 mmol) of pent-1-yn-5-ol were dissolved in 50 ml of dry DMF, and 10.10 g (149 mmol, 2.5 eq.) of imidazole and 9.40 g (62.4 mmol, 1.1 eq.) of TBS-Cl were added. After 12 hours of stirring at RT, 250 ml of water were added and the mixture was extracted with 3×150 ml of MTBE. The organic phase was washed 3× with in each case 100 ml of water and then dried over $MgSO_4$. Purification by column chromatography gave 11.10 g (53.5 mmol, 90%) of 5-(tert-butyldimethylsiloxy)pent-1-yne as a colorless oil.

$C_9H_{22}O_2Si_1$, MW 190.36 g/mol; TLC (cyclohexane/EA 10:1): $R_f$=0.38.

$^1$H-NMR (300 MHz; $CDCl_3$): δ [ppm]=0.01 (s, 6H, $SiMe_2$); 0.85 (s, 9H, Si—$CMe_3$); 1.88 (t, $^4$J=3.5 Hz, 1H, H-1); 2.22 (dt, $^4$J=3.5 Hz, $^3$J=7 Hz, 2H, H-3); 3.65 (t, $^3$J=6 Hz, 2H, H-5).

$^{13}$C-NMR (75 MHz; $CDCl_3$): δ [ppm]=−5.8 (q, $OSiMe_2$); 14.8 (t, C-3); 18.3 (s, —$OCMe_3$); 25.9 (q, —$OCMe_3$); 31.5 (t, C-4); 61.4 (t, C-5); 83.1 (s,); 68.2 (d, C-1); 84.2 (s, C-2).

Example 12

Preparation of tert-butyl 1-{2'-[6"-(tert-butyldimethylsilanyloxy)-1"-hydroxyhex-2"-ynyl]-6'-methoxybenzyl}-3-methoxy-9,10-dioxo-9,10-dihydroanthracene-2-carboxylate

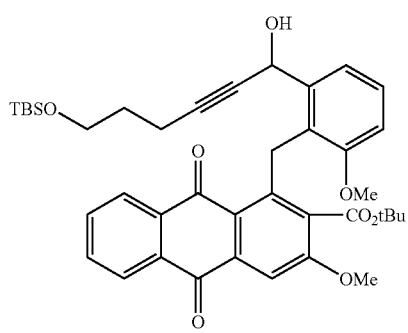

At 0° C., 0.8 ml of n-BuLi (1.23 mmol, 1.6 molar in hexane) was added to a solution of 5-(tert-butyldimethylsilyloxy)pent-1-yne (1.44 mmol) in THF (4 ml). After 15 minutes, the mixture was cooled to −60° C., and 350 mg of ClTi(Oi-Pr)$_3$ (1.31 mmol) were added. After 90 minutes, a solution of 200 mg of tert-butyl 1-(2'-formyl-6'-methoxybenzyl)-3-methoxy-9,10-dioxo-9,10-dihydroanthracene-2-carboxylate (0.4 mmol) in 6 ml of THF was injected, and stirring was continued for a further 30 minutes. The mixture was warmed to −20° C. and then stirred for another 15 hours, and finally, saturated NH$_4$Cl solution was added. The aqueous phase was extracted 2× with CH$_2$Cl$_2$, and the combined organic phases were dried over MgSO$_4$. Work-up by column chromatography (CHCl$_3$/EA 95:5) gave the addition product tert-butyl 1-{2'-[6"-(tert-butyldimethylsilanyloxy)-1"-hydroxyhex-2"-ynyl]-6'-methoxybenzyl}-3-methoxy-9,10-dioxo-9,10-dihydroanthracene-2-carboxylate in the form of a yellow oil (260 mg, 0.38 mmol, 93%).

C$_{40}$H$_{48}$O$_8$Si, MW 684.89 g/mol; TLC (CHCl$_3$/EtOAc 95:5): R$_f$=0.36.

$^1$H-NMR (250 MHz; CDCl$_3$): δ [ppm]=0.01 (s, 6H, Me$_2$Si); 0.86 (s, 9H, Me$_3$C—Si); 1.41 (s, 9H, —OCMe$_3$); 1.71 (q, 2H, —CH$_2$—CH$_2$—CH$_2$—); 2.31 (t, 2H, TBSO—(CH$_2$)$_2$—CH$_2$—); 3.38 (s, 3H, —OMe at C-3); 3.65 (t, 2H, TBSO—CH$_2$—); 4.01 (s, 3H, —OMe at C-6'); 4.54 (d, 1H, CH$_2$ at C-1); 4.81 (d, 1H, CH$_2$ at C-1); 5.86 (d, 1H, —HC—OH); 6.68 (d, 1H, H-5'); 7.15 (t, 1H, H-4'); 7.43 (d, 1H, H-3'); 7.60-7.69 (m, 2H, H-6, H-7); 7.76 (s, 1H, H-4); 7.90-8.05/8.10-8.30 (m, every 1H, H-5/H-8).

$^{13}$C-NMR (250 MHz; CDCl$_3$): δ [ppm]=−5.4 (q, Me$_2$Si); 15.4 (t, TBSO—(CH$_2$)$_2$—CH$_2$—); 18.3 (s, Me$_3$C—Si); 25.9 (q, Me$_3$C—Si); 28.0 (q, —OCMe$_3$); 30.5 (t, C-11); 31.6 (t, —CH$_2$—CH$_2$—CH$_2$—); 55.5 (q, —OMe at C-3); 56.3 (q, —OMe at C-6'); 61.7 (t, TBSO—CH$_2$—); 62.2 (d, CHOH); 80.4 (s, —OCMe$_3$); 83.0 (s, —C≡C—); 86.2 (s, —C≡C—); 107.3 (d, Ph); 111.3 (d, Ph); 120.3 (d, Ph); 125.6 (s, Ph); 126.4 (d, Ph); 127.2 (d, Ph); 127.2 (d, Ph); 132.2 (d, Ph); 133.1 (d, Ph); 134.2 (d, Ph); 135.0 (s, Ph); 136.9 (s, Ph); 141.3 (s, Ph); 145.2 (s, Ph); 157.7 (s, Ph); 159.6 (s, Ph); 166.4 (s, CO$_2^t$Bu); 183.5 (s, C=O); 183.8 (s, C=O).

Example 13

Preparation of tert-butyl-(3-methoxymethoxypent-4-ynyloxy)dimethylsilane

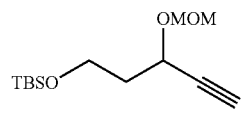

0.5 g of 5-(tert-butyldimethylsilanyloxy)pent-1-yn-3-ol (2.33 mmol) was dissolved in 15 ml of DCM, and 1.22 ml of $^i$Pr$_2$EtN (7.00 mmol) and 0.53 ml of chloromethyl methyl ether (7.00 mmol) were then added at 25° C. After 15 hours, the reaction was terminated by addition of 10 ml of water, and the mixture was extracted with 10 ml of DCM. Drying of the organic phase, removal of the solvent and work-up by column chromatography gave 0.45 g (1.75 mmol, 75%) of the product tert-butyl-(3-methoxymethoxypent-4-ynyloxy)dimethylsilane as a colorless oil.

C$_{13}$H$_{26}$O$_3$Si, MW 258.43 g/mol; TLC (cyclohexane/EtOAc, 9:1): R$_f$=0.49.

$^1$H-NMR (250 MHz; CDCl$_3$): δ [ppm]=0.03 (s, 6H, Me$_2$Si); 0.87 (s, 9H, Me$_3$C—Si); 1.85-2.00 (m, 2H, —CH$_2$—CH$_2$—CH—); 2.39 (d, 1H, —C≡CH—); 3.36 (s, 3H, —OCH$_2$OMe); 3.74 (m, 2H, TBSO—CH$_2$—); 4.50 (m, 1H, CHOMOM); 4.59 (d, 1H, —OCH$_2$OMe); 4.90 (d, 1H, —OCH$_2$OMe).

$^{13}$C-NMR (250 MHz; CDCl$_3$): δ [ppm]=−5.4 (q, (Me$_3$)$_2$Si); 18.2 (s, Me$_3$C—Si); 25.9 (q, Me$_3$C—Si); 38.9 (t, —CH$_2$—CH$_2$—CH$_2$—); 55.6 (q, —OCH$_2$OMe); 58.8 (t, TBSO—CH$_2$—); 62.4 (d, MOMOCH—); 73.5 (s, —C≡C—); 94.2 (q, —OCH$_2$OMe).

Example 14

Preparation of tert-butyl 6"-(tert-butyldimethylsilanyloxy)-1"-hydroxy-4"-methoxymethoxyhex-2"-ynyl]-6'-methoxybenzyl}-3-methoxy-9,10-dioxo-9,10-dihydroanthracene-2-carboxylate

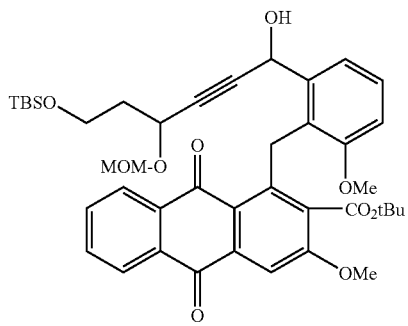

Analogously to example 12, tert-butyl 1-(2'-formyl-6'-methoxybenzyl)-3-methoxy-9,10-dioxo-9,10-dihydroanthracene-2-carboxylate was reacted with tert-butyl-(3-methoxymethoxypent-4-ynyloxy)dimethylsilane. After work-up by column chromatography on silica gel (CHCl$_3$/EA 95:5), the addition product tert-butyl 6"-(tert-butyldimethylsilanyloxy)-1"-hydroxy-4"-methoxymethoxyhex-2"-ynyl]-6'-methoxybenzyl}-3-methoxy-9,10-dioxo-9,10-dihydroanthracene-2-carboxylic acid could be obtained in the form of a yellow oil (230 mg, 0.31 mmol, 75%).

$C_{42}H_{52}O_{10}Si$, MW 744.94 g/mol; TLC ($CHCl_3$/EtOAc 95:5): $R_f$=0.31.

$^1$H-NMR (250 MHz; $CDCl_3$): δ [ppm]=0.02 (s, 6H, $Me_2Si$); 0.87 (s, 9H, $Me_3C$—Si); 1.41 (s, 9H, —$OCMe_3$); 1.96 (m, 2H, —$CH_2$—$CH_2$—CH—); 3.34 (s, 3H, —$OCH_2OMe$); 3.38 (s, 3H, —OMe at C-3); 3.74 (m, 2H, TBSO—$CH_2$—); 4.01 (s, 3H, —OMe at C-6'); 4.58 (m, 3H, $CH_2$ at C-1, —$OCH_2OMe$, CHOMOM); 4.81 (d, 1H, $CH_2$ at C-1); 4.92 (d, 1H, —$OCH_2OMe$); 5.94 (d, 1H, —HC—OH); 6.66 (d, 1H, H-5'); 7.15 (t, 1H, H-4'); 7.40 (d, 1H, H-3'); 7.60-7.69 (m, 2H, H-6, H-7); 7.76 (s, 1H, H-4); 7.93-7.98/8.14-8.18 (m, every 1H, H-5/H-8).

$^{13}$C-NMR (250 MHz; $CDCl_3$): δ [ppm]=–5.4 (q, $Me_2Si$); 18.2 (s, $Me_3C$—Si); 25.9 (q, $Me_3C$—Si); 28.1 (q, —$OCMe_3$); 30.4 (t, C-11); 38.9 (t, —$CH_2$—$CH_2$—$CH_2$—); 55.5, 55.6 (q, —OMe at C-3 and q, —$OCH_2OMe$); 56.3 (q, —OMe at C-6'); 59.0 (t, TBSO—$CH_2$—); 62.0 (d, CHOH); 62.7 (d, MOMOCH—); 83.1 (s, —$OCMe_3$); 84.6 (s, —C≡C—); 85.8 (s, —C≡C—); 94.2 (q, —$OCH_2OMe$); 107.3 (d, Ph); 111.5 (d, Ph); 120.5 (d, Ph); 125.6 (s, Ph); 125.7 (s, Ph); 126.4 (d, Ph); 127.2 (d, Ph); 127.3 (d, Ph); 132.3 (s, Ph); 133.1 (d, Ph); 134.2 (d, Ph); 135.1 (s, Ph); 136.9 (s, Ph); 140.7 (s, Ph); 144.7 (s, Ph); 157.8 (s, Ph); 159.6 (s, Ph); 166.4 (s, $CO_2^tBu$); 183.1 (s, C=O); 183.5 (s, C=O).

Example 15

Preparation of tert-butyl 1-{2'-[6"-(tert-butyldimethylsilanyloxy)-1"-hydroxyhexyl]-6'-methoxybenzyl}-3-methoxy-9,10-dioxo-9,10-dihydroanthracene-2-carboxylate

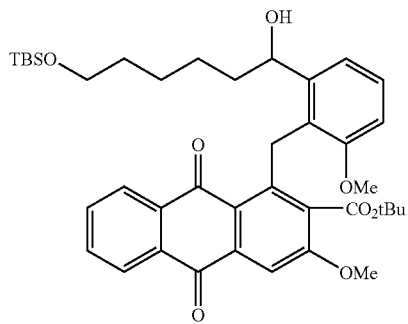

Palladium on carbon (5% by weight) was added to a solution of 0.12 g (0.18 mmol) of tert-butyl 1-{2'-[6"-(tert-butyldimethylsilanyloxy)-1"-hydroxyhex-2"-ynyl]-6'-methoxybenzyl}-3-methoxy-9,10-dioxo-9,10-dihydroanthracene-2-carboxylate (example 12) in 40 ml of EA (weight ratio 1:10 catalyst/substrate). The mixture was stirred under an $H_2$ atmosphere for 2 hours, the catalyst was then filtered off, the solvent was removed and the product was purified by column chromatography. This gave 0.11 g (0.16 mmol, 90%) of the product tert-butyl 1-{2'-[6"-(tert-butyldimethylsilanyloxy)-1"-hydroxyhexyl]-6'-methoxybenzyl}-3-methoxy-9,10-dioxo-9,10-dihydroanthracene-2-carboxylate as a yellow oil.

$C_{40}H_{52}O_8Si$, MW 688.92 g/mol; TLC (cyclohexane/EtOAc, 7:3): $R_f$=0.48.

$^1$H-NMR (250 MHz; $CDCl_3$): δ [ppm]=0.00 (s, 6H, $Me_2Si$); 0.85 (s, 9H, $Me_3C$—Si); 1.35-1.45 (m, 4H, —$CH_2$—$CH_2$—$CH_2$—CH—); 1.41 (s, 9H, —$OCMe_3$); 1.51-1.59 (m, 2H, —$CH_2$—CH—); 1.97-2.38 (m, 2H, TBSO—$CH_2$—$CH_2$—); 3.31 (s, 3H, —OMe at C-3); 3.55 (t, 2H, TBSO—$CH_2$—); 4.00 (s, 3H, —OMe at C-6'); 4.44-4.84 and 5.45-6.00 (m, 3H, $CH_2$ at C-1, CHOH); 6.57 (d, 1H, H-5'); 7.08-7.20 (m, 2H, H-5', H-4'); 7.62-7.68 (m, 2H, H-6, H-7); 7.75 (s, 1H, H-4); 7.92-7.98/8.13-8.19 (m, every 1H, H-5/H-8).

$^{13}$C-NMR (250 MHz; $CDCl_3$): δ [ppm]=–5.3 (q, $Me_2Si$); 18.3 (s, $Me_3C$—Si); 24.1 (t, —$CH_2$—); 25.9 (q, $Me_3C$—Si); 26.1 (t, —$CH_2$—); 28.0 (q, —$OCMe_3$); 30.4 (t, C-11); 32.4 (t, —$CH_2$—); 32.8 (t, —$CH_2$—); 55.4 (q, —OMe at C-3); 56.3 (q, —OMe at C-6'); 62.3 (t, TBSO—$CH_2$—); 66.7 (d, CHOH); 82.8 (s, —$OCMe_3$); 107.1 (d, Ph); 110.5 (d, Ph); 119.4 (d, Ph); 125.1 (s, Ph); 125.7 (s, Ph); 126.4 (d, Ph); 127.2 (d, Ph); 131.1 (d, Ph); 132.3 (s, Ph); 132.6 (d, Ph); 133.1 (d, Ph); 134.2 (d, Ph); 135.2 (s, Ph); 136.8 (s, Ph); 144.5 (s, Ph); 145.5 (s, Ph); 157.7 (s, Ph); 159.5 (s, Ph); 166.3 (s, $CO_2^tBu$); 183.3 (s, C=O); 183.5 (s, C=O).

Example 16

Preparation of tert-butyl 1-[2'-(5"-carboxypentanoyl)-6'-methoxybenzyl]-3-methoxy-9,10-dioxo-9,10-dihydroanthracene-2-carboxylate Via Jones Oxidation

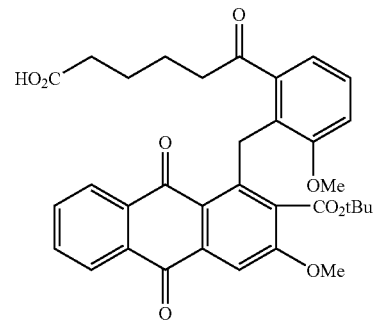

At 0° C., 5 equivalents of Jones reagent were added dropwise over a period of 5 minutes to a solution of 47 mg (0.07 mmol) of tert-butyl 1-{2'-[6"-(tert-butyldimethylsilanyloxy)-1"-hydroxyhexyl]-6'-methoxybenzyl}-3-methoxy-9,10-dioxo-9,10-dihydroanthracene-2-carboxylate (example 15) in 4 ml of acetone. The mixture was stirred initially at 0° C. for 1 hour and then at RT for 3 hours. Excess oxidizing agent was destroyed by addition of 2-propanol. After dilution with 10 ml of water, the mixture was extracted with 3×10 ml of EA. The organic phases were dried over $Na_2SO_4$, and the solvent was removed. Purification by column chromatography gave 21 mg (0.04 mmol, 52%) of the product tert-butyl 1-[2"-(5"-carboxypentanoyl)-6'-methoxybenzyl]-3-methoxy-9,10-dioxo-9,10-dihydroanthracene-2-carboxylate as a yellowish oil.

$C_{34}H_{34}O_9$, MW 586.63 g/mol; TLC ($CHCl_3$/MeOH 95:5): $R_f$=0.35.

Example 17

Preparation of tert-butyl 1-{2'-[6"-(tert-butyldimethylsilanyloxy)hexanoyl]-6'-methoxybenzyl}-3-methoxy-9,10-dioxo-9,10-dihydroanthracene-2-carboxylate Via Swern Oxidation

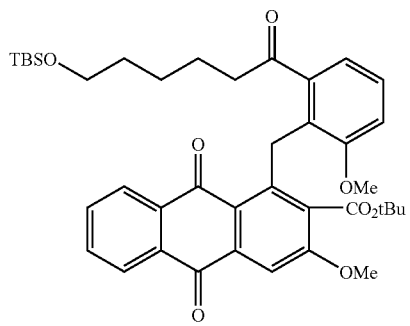

At −78° C., 33 mg of DMSO (0.42 mmol) were added to a solution of 27 mg (0.21 mmol) of oxalyl chloride in 2 ml of DCM. After 5 minutes, 48 mg (0.07 mmol) of tert-butyl 1-{2'-[6"-(tert-butyldimethylsilanyloxy)-1"-hydroxyhexyl]-6-methoxybenzyl}-3-methoxy-9,10-dioxo-9,10-dihydroanthracene-2-carboxylate, dissolved in 3 ml of DCM, were added. After a further 15 minutes, 85 mg (0.84 mmol) of NEt$_3$ were finally added, and the solution was warmed to RT and stirred for 15 hours. After the addition of 10 ml of saturated NH$_4$Cl solution, the organic phase was separated off, and dried over Na$_2$SO$_4$ and filtered, and the solvent was removed. Purification by column chromatography gave 34 mg (0.05 mmol, 72%) of the product tert-butyl 1-{2'-[6"-(tert-butyldimethylsilanyloxy)hexanoyl]-6'-methoxybenzyl}-3-methoxy-9,10-dioxo-9,10-dihydroanthracene-2-carboxylate as a yellow oil.

C$_{40}$H$_{50}$O$_8$Si, MW 686.91 g/mol; TLC (CHCl$_3$/EtOAc 95:5): R$_f$=0.39.

$^1$H-NMR (250 MHz; CDCl$_3$): δ [ppm]=0.00, 0.02 (2s, 6H, Me$_2$Si); 0.84, 0.86 (2s, 9H, Me$_3$C—Si); 1.38, 1.47 (2s, 9H, —OCMe$_3$); 1.40-1.59 (m, 4H, —CH$_2$—CH$_2$—CH$_2$—CH—); 1.60-1.80 (m, 2H, TBSO—CH$_2$—CH$_2$—); 2.44, 3.03 (2t, 2H, —CH$_2$—CO—); 3.44, 3.64 (2s, 3H, —OMe at C-3); 3.53, 3.59 (2t, 2H, TBSO—CH$_2$—); 4.00 (s, 3H, —OMe at C-6'); 4.71, 4.73 (m, 2H, CH$_2$ at C-1); 6.74, 6.82 (2d, 1H, H-5'); 6.94, 7.02, 7.07, 7.14 (4d, 2H, H-5', H-4'); 7.62-7.69 (m, 2H, H-6, H-7); 7.72, 7.75 (2s, 1H, H-4); 7.94-8.00/8.12-8.19 (m, every 1H, H-5/H-8).

We claim:

1. A process for preparing a mumbaistatin derivative of formula (I) or a salt thereof

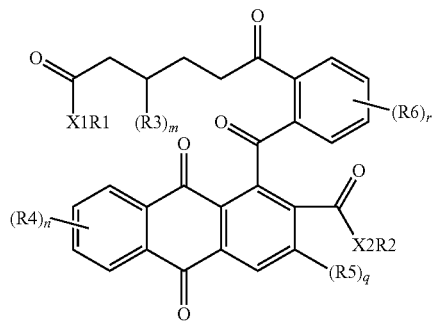

wherein:

R1 and R2 are independently H, (C$_1$-C$_6$)-alkyl or benzyl;

R3, R4 and R5 are independently OH, O—(C$_1$-C$_6$)-alkyl, O-benzyl or O-acyl;

R6 is OH, halogen, (C$_1$-C$_6$)-alkyl, O—(C$_1$-C$_6$)-alkyl, phenyl, benzyl, O-phenyl, O-benzyl, or O-acyl;

X1 and X2 are independently O, NH, N(C$_1$-C$_6$)-alkyl or S; and m, n, q and r are independently 0 or 1;

comprising (1) reacting a compound of formula (II)

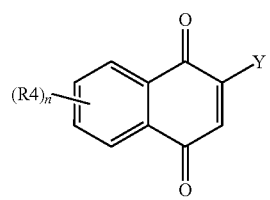

wherein Y is a leaving group selected from the group consisting of Hal, OTs, OTf and OMs, with a compound of formula (III),

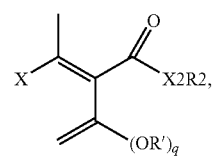

wherein X is an electron-pushing group and R' is (C$_1$-C$_6$)-alkyl or [(C$_1$-C$_6$)-alkyl]$_3$silyl, in a [2+4]cycloaddition, and subsequently reacting with a suitable acid to give a compound of formula (IV)

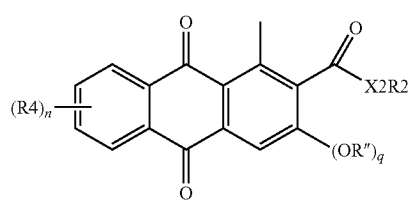

wherein R" is H or (C$_1$-C$_6$)-alkyl;

(2) halogenating the compound of formula (IV), or an etherified or acylated compound thereof when q is 1 and R" is H, to give a compound of formula (V), wherein the etherified compound is prepared by etherifying the compound of formula (IV) with a (C$_1$-C$_6$)-alkyl halide compound or a benzyl halide compound, and the acylated compound is prepared by esterifying the compound of formula (IV) with an acyl halide compound, or
reacting the compound of formula (V) with an organometallic compound of formula (VI')

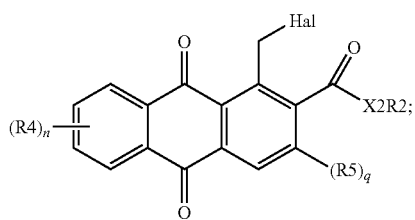
(V)

(3) reacting the compound of formula (V) with an organometallic compound (VI)

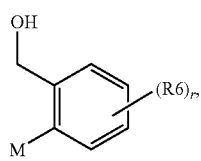
(VI)

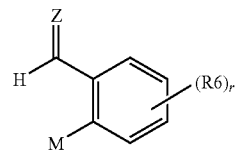
(VI')

wherein M is as defined for compound (VI) and Z is O—($C_1$-$C_6$)-alkylene-O, in the presence of a transition metal catalyst, to give a compound of formula (VII'), wherein M is Sn[($C_1$-$C_6$)-alkyl]$_3$, B(OH)$_2$, B(OR)$_2$, BF$_3^-$, ZnHal or MgHal, and (OR)$_2$ is [O—($C_1$-$C_6$)-alkyl]$_2$ or a 1,2-vicinal diol, in the presence of a transition metal catalyst, to give a compound of formula (VII),

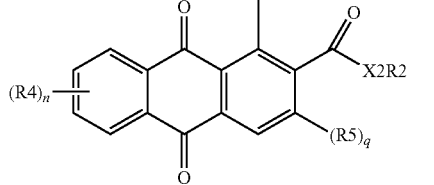
(VII)

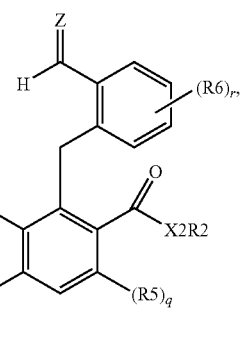
(VII')

and then hydrolyzing the compound of formula (VII') with a suitable acid to give a compound of formula (VIII),
or
when X2R2 is OH, esterifying the compound of formula (V) with the compound (VI) to give a compound of formula (VII"), and then oxidizing the compound of formula (VII) to give a compound of formula (VIII),

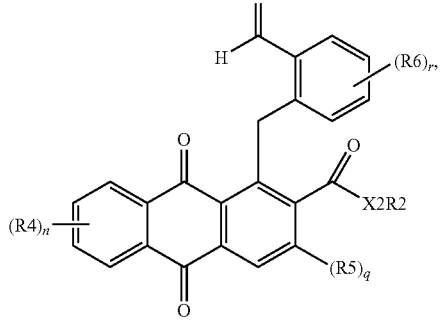
(VIII)

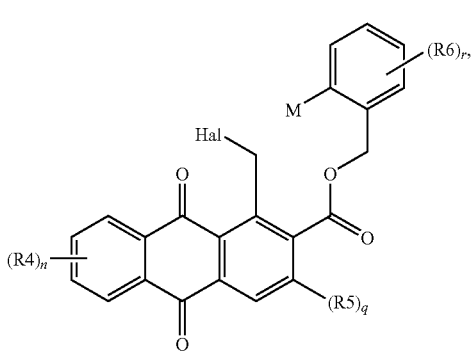
(VII")

converting the compound of formula (VII"), in the presence of a transition metal catalyst, into a compound of formula (VII'''),

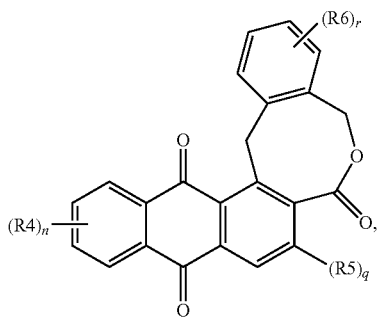

hydrolyzing the compound of formula (VII''') under a basic or acidic condition to give a compound of formula (VII) wherein X2R2 is OH, oxidizing the compound formula (VII) to give a compound of formula (VIII) wherein X2R2 is OH, and optionally converting the compound of formula (VIII) wherein X2R2 is OH into a compound of formula (VIII) wherein X2 is O, NH, N(C$_1$-C$_6$)-alkyl or S, and R2 is H, (C$_1$-C$_6$)-alkyl or benzyl, provided that X2R2 is not OH;

(4) reacting the compound of formula (VIII) with a compound of formula (IX)

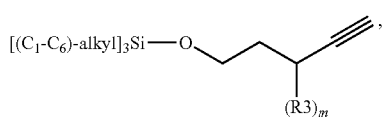

to give a compound of formula (X),

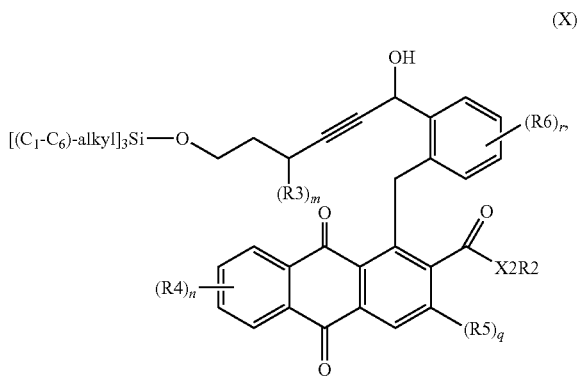

(5) converting the compound of formula (X) into a compound of formula (XI) by hydrogenating the triple bond to a single bond and removing the [(C$_1$-C$_6$)-alkyl]$_3$Si group,

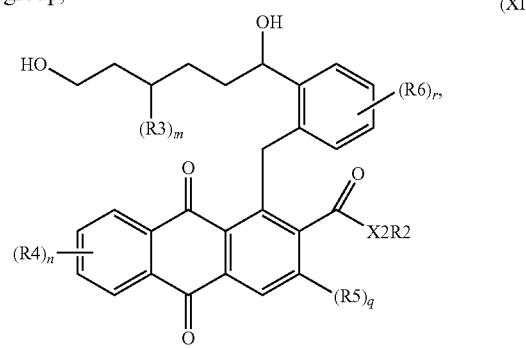

(6) optionally oxidizing the compound of formula (XI) to give a compound of formula (XII),

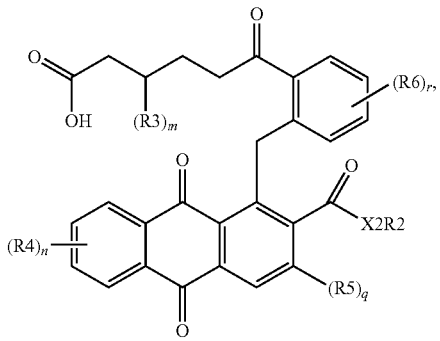

(7) oxidizing the compound of formula (XI) or the compound of formula (XII) to give the compound of formula (I) wherein X1R1 is OH, and (8) optionally converting the compound of formula (I) wherein X1R1 is OH into the compound of formula (I) wherein X1 is O, NH, N(C$_1$-C$_6$)-alkyl or S, and R1 is H, (C$_1$-C$_6$)-alkyl or benzyl, or a salt thereof, provided that X1R1 is not OH.

2. The process according to claim 1, wherein the compound of formula (I) is a compound of formula (I-A)

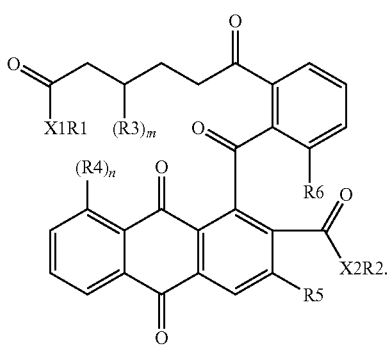

3. The process according to claim 2, wherein in the compound of formula (I-A)
X1R1 is OH or O—(C$_1$-C$_6$)-alkyl,
X2R2 is OH,
R3 is OH,
R4 is OH or O—(C$_1$-C$_6$)-alkyl,
R5 is OH or O—(C$_1$-C$_6$)-alkyl,
R6 is OH or O—(C$_1$-C$_6$)-alkyl, and
m and n are independently 0 or 1.

4. The process according to claim 1, wherein X is [(C$_1$-C$_6$)-alkyl]$_3$silyloxy.

5. The process according to claim 1, wherein X is [methyl]$_3$silyloxy.

6. The process according to claim 1, wherein (OR)$_2$ is pinacol or catechol.

7. The process according to claim 1, wherein the transitional metal catalyst is Pd, Ni or Ge catalyst.

8. The process according to claim 1, wherein Z is O—(CH$_2$—CH$_2$)—O.

9. A compound of formula (IV)

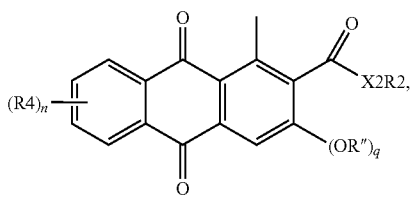

where R″ is ($C_1$-$C_6$)-alkyl;
R2 is H, ($C_1$-$C_6$)-alkyl of benzyl;
R4 is O—($C_1$-$C_6$)-alkyl, O-benzyl or O-acyl;
X2 is O, NH, N($C_1$-$C_6$)-alkyl or S; and
n and q are independently 0 or 1.

10. The compound according to claim 9, wherein X2R2 is OH or O—($C_1$-$C_6$)-alkyl, R4 is OH or O—($C_1$-$C_6$)-alkyl, and n and q are independently 0 or 1.

11. The compound according to claim 10, wherein n is 0 or 1, and q is 1.

12. A compound of formula (V),

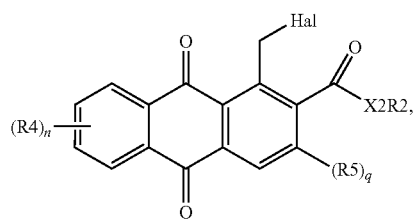

wherein R2, R4, R5, X2, Hal, n and q are as defined in claim 1.

13. The compound according to claim 12, wherein X2R2 is OH or O—($C_1$-$C_6$)-alkyl, R4 and R5 are independently OH or O—($C_1$-$C_6$)-alkyl, n and q are independently 0 or 1, and Hal is chlorine, bromine or iodine.

14. The compound according to claim 13, wherein X2R2 is OH or O—($C_1$-$C_6$)-alkyl, R4 and R5 are O($C_1$-$C_6$)-alkyl, n is 0 or 1, q is 1, and Hal is chlorine, bromine or iodine.

15. A compound of formula (VII),

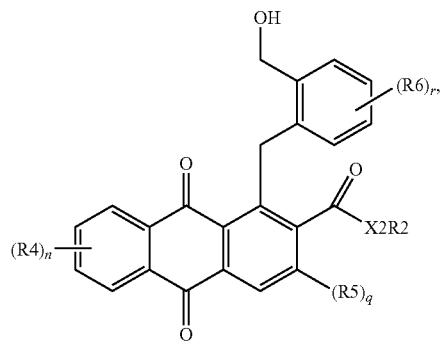

wherein R2, R4, R5, R6, X2, n, q and r are as defined in claim 1.

16. The compound according to claim 15, which is a compound of formula (VII-A)

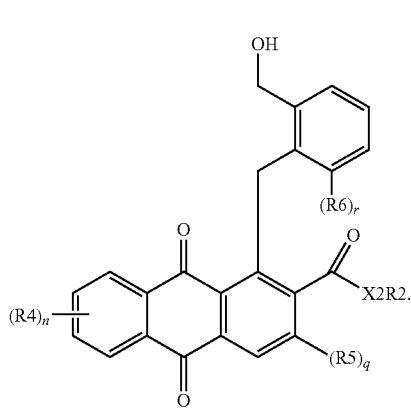

17. The compound according to claim 15, wherein X2R2 is OH or O—($C_1$-$C_6$)-alkyl, R4, R5 and R6 are independently OH or O—($C_1$-$C_6$)-alkyl, and n, q and r are independently 0 or 1.

18. The compound according to claim 15, wherein X2R2 is OH or O—($C_1$-$C_6$)-alkyl, R4, R5 and R6 are O—($C_1$-$C_6$)-alkyl, n is 0 or 1, and q and r are 1.

19. A compound of formula (VII′)

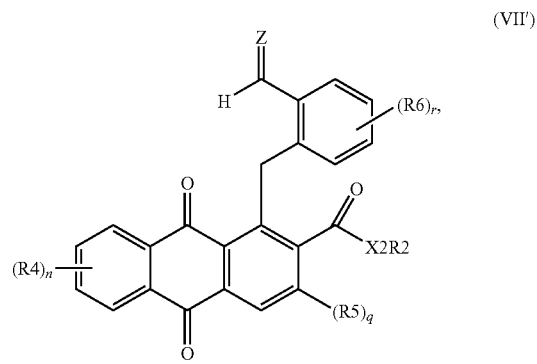

wherein Z is O—($C_1$-$C_6$)-alkylene-O, and R2, R4, R5, R6, X2, n, q and r are as defined in claim 1.

20. The compound according to claim 19, which is a compound of formula (VII′-A)

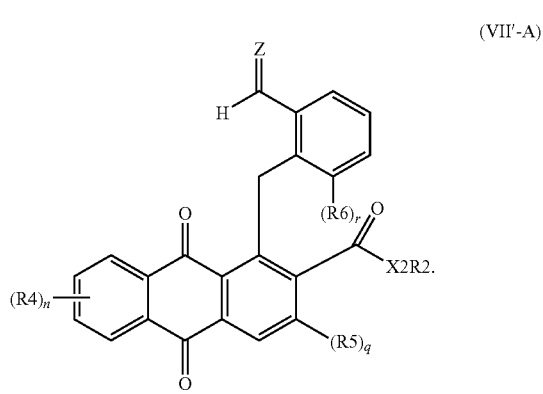

21. The compound according to claim 19, wherein X2R2 is OH or O—($C_1$-$C_6$)-alkyl, R4, R5 and R6 are independently OH or O—($C_1$-$C_6$)-alkyl, and n, q and r are independently 0 or 1.

22. The compound according to claim 19, wherein X2R2 is OH, R4, R5 and R6 are O—($C_1$-$C_6$)-alkyl, n is 0 or 1, and q and r are 1.

23. The compound according to claim 19, wherein Z is O—($CH_2$—$CH_2$)—O.

24. A compound of formula (VII″)

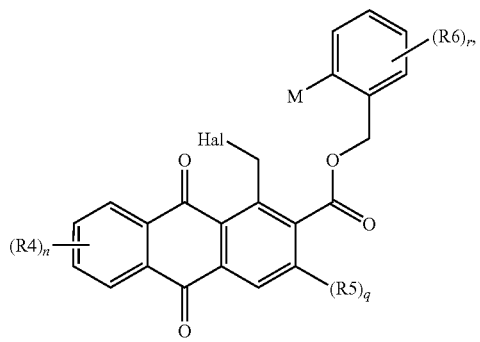

(VII″)

wherein Hal, R4, R5, R6, n, q and r are as defined in claim 1.

25. The compound according to claim 24, which is a compound of formula (VII″-A)

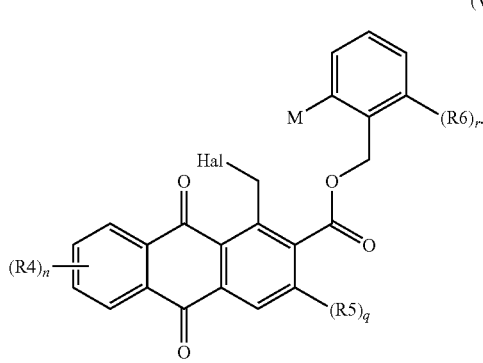

(VII″-A)

26. The compound according to claim 24, wherein R4, R5 and R6 are independently OH or O—($C_1$-$C_6$)-alkyl, Hal is chlorine, bromine or iodine, and n, q and r are independently 0 or 1.

27. The compound according to claim 24, wherein R4, R5 and R6 are O—($C_1$-$C_6$)-alkyl, Hal is chlorine or bromine, n is 0 or 1, and q and r are 1.

28. A compound of formula (VII‴)

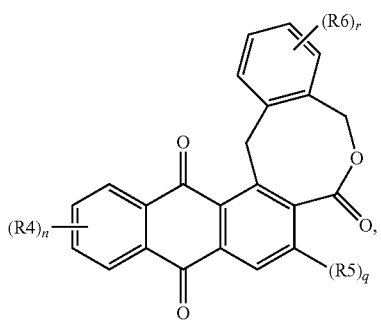

(VII‴)

wherein R4, R5, R6, n, q and r are as defined in claim 1.

29. The compound according to claim 28, which is a compound of formula (VII‴-A)

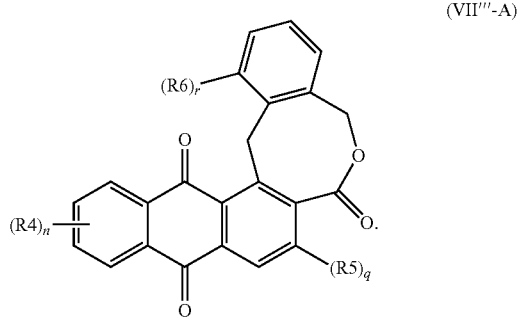

(VII‴-A)

30. The compound according to claim 28, wherein R4, R5 and R6 are independently OH or O—($C_1$-$C_6$)-alkyl, and n, q and r are independently 0 or 1.

31. The compound according to claim 28, wherein R4, R5 and R6 are O—($C_1$-$C_6$)-alkyl, n is 0 or 1, and q and r are 1.

32. A compound of formula (VIII),

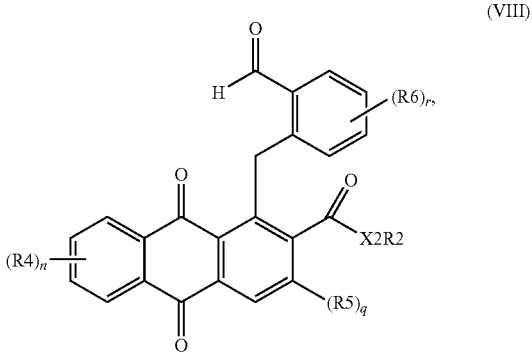

(VIII)

wherein R2, R4, R5, R6, X2, n, q and r are as defined in claim 1.

33. The compound according to claim 32, which is a compound of formula (VIII-A)

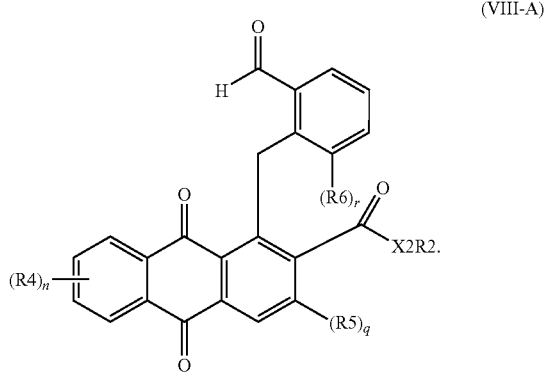

(VIII-A)

34. The compound according to claim 32, wherein X2R2 is OH or O—($C_1$-$C_6$)-alkyl, R4, R5 and R6 are independently OH or O—($C_1$-$C_6$)-alkyl, and n, q and r are independently 0 or 1.

35. The compound according to claim 32, wherein X2R2 is OH or O—(C$_1$-C$_6$)-alkyl, R4, R5 and R6 are O—(C$_1$-C$_6$)-alkyl, n is 0 or 1, and q and r are 1.

36. A compound of formula (XI)

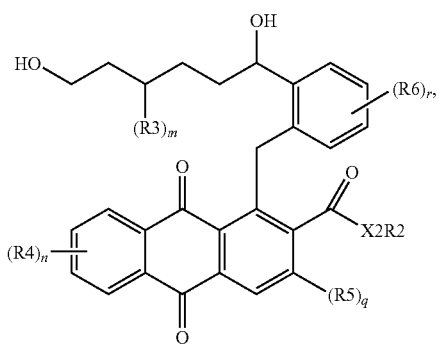
(XI)

wherein R2, R3, R4, R5, R6, X2, m, n, q and r are as defined in claim 1.

37. The compound according to claim 36, which is a compound of formula (XI-A)

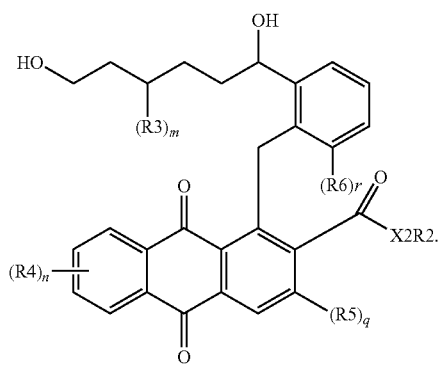
(XI-A)

38. The compound according to claim 36, wherein X2R2 is OH or O—(C$_1$-C$_6$)-alkyl, R4, R5 and R6 are independently OH or O—(C$_1$-C$_6$)-alkyl, and n, q and r are independently 0 or 1.

39. A compound of formula (XII)

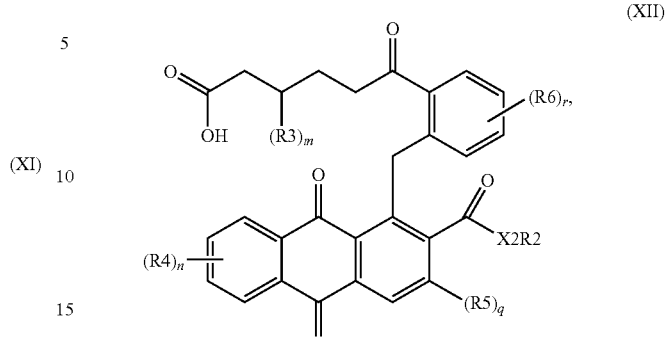
(XII)

wherein
R2 is H, (C$_1$-C$_6$)-alkyl or benzyl,
R3 and R4 are independently OH, O—(C$_1$-C$_6$)-alkyl, phenyl, benzyl, O-benzyl, or O-acy;
R5 is O—(C$_1$C$_6$)-alky, O-benzyl or O-acyl,
R6 is OH, halogen, (C$_1$-C$_6$)-alky, phenyl, benzyl, O-phenyl, O-benzyl, or O-acyl,
X2 is O, NH, N(C$_1$-C$_6$)-alkyl or S, and,
m, n, q and r are as defined in claim 1.

40. The compound according to claim 39, which is a compound of formula (XII-A)

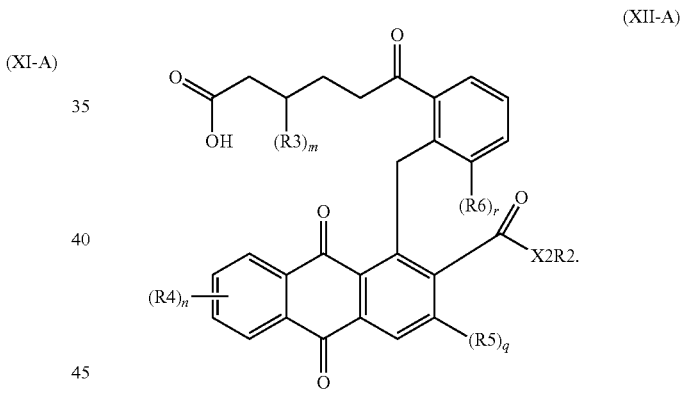
(XII-A)

41. The compound according to claim 39, wherein X2R2 is OH or O—(C$_1$-C$_6$)-alkyl, R4, R5 and R6 are independently OH or O—(C$_1$-C$_6$)-alkyl, and n, q and r are independently 0 or 1.

* * * * *